US010646199B2

(12) United States Patent
Pelissier et al.

(10) Patent No.: US 10,646,199 B2
(45) Date of Patent: May 12, 2020

(54) SYSTEMS AND METHODS FOR REMOTE GRAPHICAL FEEDBACK OF ULTRASOUND SCANNING TECHNIQUE

(71) Applicant: Clarius Mobile Health Corp., Burnaby (CA)

(72) Inventors: Laurent Pelissier, North Vancouver (CA); Trevor Hansen, Vancouver (CA); Jacob McIvor, Vancouver (CA); Benjamin Eric Kerby, Richmond (CA); David Glenn Willis, Woodinville, WA (US); Narges Afsham, Coquitlam (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 1213 days.

(21) Appl. No.: 14/887,157

(22) Filed: Oct. 19, 2015

(65) Prior Publication Data
US 2017/0105701 A1    Apr. 20, 2017

(51) Int. Cl.
*A61B 8/00*     (2006.01)
*G16H 30/40*    (2018.01)
*G16H 80/00*    (2018.01)
*G16H 50/20*    (2018.01)

(52) U.S. Cl.
CPC ............ *A61B 8/4254* (2013.01); *A61B 8/461* (2013.01); *A61B 8/467* (2013.01); *A61B 8/565* (2013.01); *G16H 30/40* (2018.01); *G16H 50/20* (2018.01); *G16H 80/00* (2018.01)

(58) Field of Classification Search
CPC .................................................... A61B 5/0002
See application file for complete search history.

(56) References Cited

U.S. PATENT DOCUMENTS

| 5,608,849 | A | | 3/1997 | King, Jr. |
| 5,920,317 | A | | 7/1999 | McDonald |
| 5,922,018 | A | * | 7/1999 | Sarvazyan ........... A61B 1/0052 |
| | | | | 600/587 |
| 6,458,081 | B1 | | 10/2002 | Matsui et al. |
| 6,500,119 | B1 | | 12/2002 | West et al. |
| 6,705,990 | B1 | | 3/2004 | Gallant et al. |
| 7,386,730 | B2 | | 6/2008 | Uchikubo |
| 7,453,472 | B2 | | 11/2008 | Goede et al. |
| 7,549,961 | B1 | | 6/2009 | Hwang |

(Continued)

FOREIGN PATENT DOCUMENTS

WO        2014144964 A1    9/2014

OTHER PUBLICATIONS

"A tele-instruction system for ultrasound probe operation based on shared AR technology" by T. Suenaga et al. Proc. 23rd Annual EMBS Int. Conf. pp. 3765-3768. 2001.*

(Continued)

*Primary Examiner* — Jeffrey G Hoekstra
*Assistant Examiner* — Jason M Ip
(74) *Attorney, Agent, or Firm* — Julian Ho

(57) ABSTRACT

An apparatus and method for providing remote expert feedback to an operator of an ultrasound imaging machine. The remote feedback consists of graphical icons that are dragged and dropped onto a video stream of the patient being scanned or the ultrasound image being captured and shared in real-time with the local operator to help improve their scanning technique.

24 Claims, 11 Drawing Sheets

(56) References Cited

U.S. PATENT DOCUMENTS

| | | | |
|---|---|---|---|
| 7,597,644 B2 | 10/2009 | Rodgers, II | |
| 8,069,420 B2 | 11/2011 | Plummer | |
| 8,172,753 B2* | 5/2012 | Halmann | A61B 8/00 128/916 |
| 8,297,983 B2 | 10/2012 | Savitsky et al. | |
| 9,007,476 B2 | 4/2015 | Glover | |
| 9,021,358 B2 | 4/2015 | Amble et al. | |
| 2003/0046562 A1 | 3/2003 | Uchikubo | |
| 2004/0019270 A1* | 1/2004 | Takeuchi | A61B 8/14 600/407 |
| 2005/0049495 A1 | 3/2005 | Sumanaweera et al. | |
| 2005/0073575 A1* | 4/2005 | Thacher | H04N 7/141 348/14.13 |
| 2007/0242069 A1* | 10/2007 | Matsue | G06F 19/321 345/428 |
| 2008/0194960 A1* | 8/2008 | Randall | A61B 8/00 600/459 |
| 2009/0125147 A1 | 5/2009 | Wang et al. | |
| 2009/0189988 A1 | 7/2009 | Jia et al. | |
| 2009/0306509 A1 | 12/2009 | Pedersen et al. | |
| 2009/0326318 A1 | 12/2009 | Tognaccini et al. | |
| 2010/0123908 A1 | 5/2010 | Denoue et al. | |
| 2010/0222680 A1 | 9/2010 | Hamada | |
| 2010/0325546 A1 | 12/2010 | Leo et al. | |
| 2011/0267418 A1* | 11/2011 | Galindo | H04N 7/15 348/14.04 |
| 2011/0301461 A1 | 12/2011 | Anite | |
| 2011/0306025 A1 | 12/2011 | Sheehan et al. | |
| 2012/0179039 A1 | 7/2012 | Pelissier et al. | |
| 2013/0249842 A1 | 9/2013 | Varna | |
| 2013/0296707 A1 | 11/2013 | Anthony et al. | |
| 2014/0011173 A1 | 1/2014 | Tepper et al. | |
| 2014/0267660 A1 | 9/2014 | Pagoulatos et al. | |
| 2014/0282018 A1 | 9/2014 | Amble et al. | |
| 2015/0005630 A1 | 1/2015 | Jung et al. | |

OTHER PUBLICATIONS

Abstract of Stolka, P., et al., "5-DoF trajectory reconstruction for handheld ultrasound with local sensors", Ultrasonics Symposium (IUS), 2009 IEEE International, 1864-1867.
Poulsen, C., et al., "An Optical Registration Method for 3D Ultrasound Freehand Scanning", Proceedings of the IEEE Ultrasonics Symposium (2005) 2:1236-1240.
Abstract of Stolka, P., et al., "Multi-DoF probe trajectory reconstruction with local sensors for 2D-to-3D ultrasound", Biomedical Imaging: From Nano to Macro, 2010 IEEE International Symposium, 316-319.
Abstract of Goldsmith, A.M., et al., "An inertial-optical tracking system for portable, quantitative, 3D ultrasound", Ultrasonics Symposium, 2008, IUS 2008, IEEE, 45-49.
Blattman, J. (2011). 3D Model Viewer (1.2.1) [Mobile application software], available at https://play.google.com/store/apps/details?id=org.jtb.modelview&hl=en, last accessed Jan. 31, 2017.
Duke Dev (2015). HD Model Viewer (0.51). [Mobile application software], available at https://play.google.com/store/apps/details?id=com.dukedev.hdmodelviewer&hl=en, last accessed Jan. 31, 2017.
SMARTMOBILEVISION (2014). Available at http://smartmobilevision.com/, last accessed Feb. 21, 2017.
Osmo, "Masterpiece for Osmo", video published Mar. 12, 2015 by Osmo, available at https://www.youtube.com/watch?v=0upQIA6K5YI, last accessed Jan. 31, 2017.
Hitachi Medical Systems Europe, publication date unknown, "Picture in Picture (PiP)", available at http://www.hitachi-medical-systems.eu/products-and-services/ultrasound/technologies/picture-in-picture-pip.html, last accessed Jan. 31, 2017.
BKULTRASOUND, publication date unknown, SonixCam, available at https://bkultrasound.com/sonixcam/, last accessed Feb. 7, 2017.
Rajasekaran, S. and J.T. Finnoff, "An Innovative Technique for Recording Picture-in-Picture Ultrasound Videos", Journal of Ultrasound in Medicine (2013) 32.8: 1493-1497.

Abstract of Dewey, C.F. Jr., et al. "Prospects for Telediagnosis Using Ultrasound", Telemedicine Journal (1996) 2.2: 87-100.
The Telemedicine Directory, publication date unknown, "TeleUltrasound", available at http://thetelemedicinedirectory.com/lc/teleultrasound/, last accessed Feb. 7, 2017.
Remote Medical Technologies (2006-2014), iMedHD2 Teleultrasound System, available at http://www2.rmtcentral.com/capabilities/teleradiology/ultrasound/, last accessed Feb. 7, 2017.
Abstract of Pyke, J., et al., "A Tele-ultrasound System for Real-time Medical Imaging in Resource-limited Settings", Engineering in Medicine and Biology Society, 2007. EMBS 2007. 29th Annual International Conference of the IEEE, Aug. 22-26, 2007.
Abstract of McBeth, P., et al., "Simple, Almost Anywhere, With Almost Anyone: Remote Low-Cost Telementored Resuscitative Lung Ultrasound", Journal of Trauma (2011) 71.6: 1528-1535.
Mai, T.V., et al., "Feasibility of Remote Real-Time Guidance of a Cardiac Examination Performed by Novices Using a Pocket-Sized Ultrasound Device", Emergency Medicine International (2013) 627230.
Martinov, D., et al., "Image Quality in Real-Time Teleultrasound of Infant Hip Exam Over Low-Bandwidth Internet Links: a Transatlantic Feasibility Study", Journal of Digital Imaging (2013) 26: 209-216.
Sutherland, J.E., et al., "A comparison of telesonography with standard ultrasound care in a rural Dominican clinic", Journal of Telemedicine and Telecare (2009) 15.4: 191-195.
Abstract of Sublett, J.W., et al., "Design and Implementation of a Digital Teleultrasound System for Real-Time Remote Diagnosis", Proceedings of the Eighth IEEE Symposium on Computer-Based Medical Systems, Jun. 9-10, 1995.
Sutherland, J.E., et al., "Telesonography: Foundations and Future Directions", Journal of Ultrasound in Medicine (2011) 30: 517-522.
Ogedegbe, C., et al., "Development and evaluation of a novel, real time mobile telesonography system in management of patients with abdominal trauma: study protocol", BMC Emergency Medicine (2012) 12:19.
Liteplo, A.S., Noble, V.E., and Attwood, B., "Real-time video transmission of ultrasound images to an iPhone", Critical Ultrasound Journal (2010) 1: 105-110.
Abstract of McBeth, P., Hamilton, T., and Kirkpatrick, A.W., "Cost-Effective Remote iPhone-Teathered Telementored Trauma Telesonography", Journal of Trauma-Injury Infection & Critical Care (2010) 69.6: 1597-1599.
Pian, L, et al., "Potential Use of Remote Telesonography as a Transformational Technology in Underresourced and/or Remote Settings", Emergency Medicine International 2013, Article ID 986160.
Biegler, N. et al., "The feasibility of nurse practitioner-performed, telementored lung telesonography with remote physician guidance—'a remote virtual mentor'", Critical Ultrasound Journal (2013) 5.5: 1-7.
Abstract of Sharon, T. and Frank, A.J., "Utilizing multimedia technologies for interactive telesonography", RIAO '00 Content-Based Multimedia Information Access (2000) 1: 830-845.
Suenaga, T. et al., "A tele-instruction system for ultrasound probe operation based on shared AR technology", National Institute for Longevity Sciences Aichi Japan, Papers from the 23rd Annual International Conference of the IEEE Engineering in Medicine and Biology Society, Oct. 25-28, 2001.
Sheehan, F.H. et al., "Expert visual guidance of ultrasound for telemedicine", Journal of Telemedicine and Telecare (2010) 16.2: 77-82.
Nasa, "Human Research Facility Ultrasound on the International Space Station 2 (Ultrasound 2)—Feb. 15, 2017", available at https://www.nasa.gov/mission_pages/station/research/experiments/749.html, last accessed Feb. 17, 2017.
Brisson, A. et al., "A comparison of telemedicine teaching to in-person teaching for the acquisition of an ultrasound skill—a pilot project", Journal of Telemedicine and Telecare (2015) 21.4: 235-239.
Adambounou, K. et al., "A low-cost tele-imaging platform for developing countries", Frontiers in Public Health (2014) 2, 135.
Doherty, S., "Telerobotic Ultrasound Distance Imaging (TRUDI)", The world's first tele-robotic echocardiography and cardiovascular

(56) References Cited

OTHER PUBLICATIONS ultrasound system (2014), available at http://www.medstartr.com/project/detail/443, last accessed Feb. 17, 2017.

Fabien, C. (2011). Design of a Bio-Inspired 3D Orientation Coordinate System and Application in Robotised Tele-Sonography, Robot Arms, Prof. Satoru Goto (Ed.), ISBN: 978-953-307-160-2, InTech, Available from: http://www.intechopen.com/books/robot-arms/design-of-a-bio-inspired-3d-orientationcoordinate-system-and-application-in-robotised-tele-sonograp.

Medgadget, "Augmented Reality System Helps Military Surgeons Treat Wounded Warriors (VIDEO)", published Aug. 25, 2015, available at http://www.medgadget.com/2015/08/augmented-reality-system-for-helping-military-surgeons-treat-wounded-warriors-video.html, last accessed Feb. 17, 2017.

Sutherland, J.E. (2009). "Telesonography Adoption and Use to Improve the Standard of Patient Care Within a Dominican Community", Dissertation submitted to the faculty of the Virginia Polytechnic Institute and State University, Blacksburg, Virginia.

Anderson, J.G., "Social, ethical and legal barriers to E-health", International Journal of Medical Informatics (2007) 76: 480-483.

Westin, C.F. et al. (2009). "Adaptive Image Filtering", Elsevier, Inc.

\* cited by examiner

SYSTEMS AND METHODS FOR REMOTE GRAPHICAL FEEDBACK OF ULTRASOUND SCANNING TECHNIQUE

FIELD

This invention relates to ultrasound imaging systems. Particular embodiments provide probe and methods that include adaptations for providing and receiving remote feedback to an operator performing an ultrasound imaging procedure.

BACKGROUND

Ultrasound is a useful, non-invasive imaging technique capable of producing real-time images. Ultrasound imaging has an advantage over X-ray imaging in that ultrasound imaging does not involve ionizing radiation.

It can be difficult to properly capture and analyse ultrasound images. The successful use of ultrasound is dependent on highly-skilled technicians to perform the scans and experienced physicians to interpret them. It typically takes several years of training for a technician to become proficient.

In order to capture a high quality image, an operator needs to use proper scanning technique, including using the right amount of coupling medium, positioning the probe correctly relative to the patient and applying the right level of pressure to the probe.

Anatomy varies between different patients. Technicians must often use ultrasound images to fine-tune positioning of the ultrasound probe. Even experienced operators often make image-plane positioning mistakes.

In addition to scanning technique, there are a wide variety of imaging parameters that must typically be adjusted to suit the type of exam, the anatomical location, and the patient.

Trained ultrasound technicians are not universally accessible. Ultrasound could be used to improve care for more patients, especially in rural and low-resource settings, if less-skilled operators were able to perform ultrasound examinations quickly and accurately.

Examples of ultrasound systems that provide some facility for training technicians and/or providing comments on ultrasound images from a remote location are described in: U.S. Pat. Nos. 8,297,983; 9,021,358; US2005/0049495; US2011/0306025; US2013/0296707; US2014/011173; and US 2015/0005630. Some existing ultrasound systems enable a remote expert to provide communications to an inexperienced operator regarding ultrasound images.

Asynchronous techniques such as 'store and forward' are known in the art. In such a system, images are acquired, and then forwarded and stored until they can be reviewed. These types of systems still rely on a highly trained sonographer to capture the initial images, and there is still a delay between imaging and diagnosis. Furthermore, if the imaging is insufficient, the examination will need to be repeated, causing further delay.

Real-time telemedicine and tele-sonography systems are known in the art. These systems typically rely on conventional multimedia communications to enable two-way communication between the examiner and a remote expert. Typically, the ultrasound imaging data is streamed in real-time and displayed simultaneously with a video stream that provides a view of the ultrasound image displayed in real-time and in some cases with a video stream depicting the patient and the probe. U.S. Pat. No. 9,021,358 discloses simultaneously displaying ultrasound imaging data, medical data about a patient, a video stream depicting the source of the ultrasound imaging data and supplemental information on a remote graphical user interface. A remote expert can provide live voice instructions and certain other feedback to the operator.

Tele-robotic systems are also known in the art. Such systems allow a remote operator to view a real-time stream of ultrasound images and to control a robot to manipulate the probe and acquire an image. Robotic systems carry the disadvantages of a lack of portability, cost, and complexity.

There remains a need for practical and cost effective systems that can help an inexperienced operator to capture ultrasound images and/or learn better imaging techniques. There is a particular need for such systems that can work effectively with relatively low-bandwidth data connections, that are language independent, and that can provide visual feedback to help the inexperienced operator to modify and improve his or her ultrasound scanning technique.

SUMMARY

This invention has a number of different aspects that have synergy when combined but are also capable of application individually and/or in subcombinations. These aspects include, without limitation:

A method for providing visual feedback from a remote expert to an ultrasound system user comprises:
  acquiring ultrasound image data at a first location;
  acquiring ultrasound image data acquisition information at the first location;
  transmitting the ultrasound image data and ultrasound image data acquisition information to a second location;
  displaying the ultrasound image data and ultrasound image data acquisition information;
  receiving instructions to adjust imaging acquisition technique;
  transmitting instructions to adjust imaging acquisition technique to the first location
  outputting instructions to adjust imaging acquisition technique.

Another aspect provides a system comprising a medical imaging device configured to acquire ultrasound image data from a patient and a patient imaging device configured to acquire patient images (which may comprise a video stream) depicting the medical imaging device and the patient. A local user interface is in communication with the medical imaging device and patient imaging device and is configured to transmit the ultrasound image data and patient image data to a remote interface located remotely. The remote interface is configured to display the ultrasound imaging data and the patient images and receive input from a positional feedback selector. The positional feedback selector includes controls for triggering transmission of predefined messages to the local user interface. The local user interface provides feedback to the user in the form of graphical elements that correspond to the predefined messages. The graphical elements may provide specific suggestions as to how a user can modify their ultrasound scanning techniques. In some embodiments the remote interface is configured to permit a user to place the controls onto a display of the ultrasound image data or patient image data using a drag and drop gesture. This positional feedback is transmitted back to the local user interface and displayed in real-time.

Another aspect provides ultrasound imaging devices comprising a hand-holdable probe comprising a transducer; transmit and receive circuits respectively operable to drive the transducer to transmit ultrasound energy to a patient and to receive signals generated by the transducer in response to ultrasound energy received from the patient; and an image processing circuit comprising a beamformer configured to process the received signals to yield ultrasound image data. The devices further comprise a data interface connected to transmit the ultrasound image data to a remote interface and to receive signals from the remote interface, the signals including position correction messages relating to positional correction for the probe; and a display connected to display the ultrasound image data in a first display area and to display positional correction symbols determined by the messages in a second display area.

In some embodiments the positional correction symbols comprise predetermined icons stored in the ultrasound imaging device, each of the predetermined icons comprising an arrow indicating a particular desired motion of the probe. Each of the icons may include a depiction of the probe. In some embodiments the icons include one or more of: icons depicting tilting the probe forward and backward; icons depicting rocking the probe right and left; icons depicting rotating the probe clockwise and counter-clockwise; and icons depicting moving the probe to the left, right, forward and backward. In some embodiments the ultrasound imaging device is configured to discontinue display of one of the positional correction symbols by fading the displayed positional control symbol a predetermined time after commencing display of the positional control symbol.

In some embodiments the ultrasound imaging devices comprise a motion sensor and are configured to determine from the motion sensor whether or not the probe is being moved in a way corresponding to a displayed positional control symbol and to discontinue display of the positional correction symbol in response to determining from the motion sensor that the probe has been moved in the way corresponding to a displayed positional control symbol. In some embodiments the ultrasound imaging devices are configured to issue a warning signal in response to determining from the motion sensor that the probe has been not moved in the way corresponding to a displayed positional control symbol.

In an example embodiment the probe comprises a self-contained battery-powered ultrasound image acquisition device that contains the transducer, the transmit and receive circuits and the image processing circuit; the display and data interface are provided on a local user interface device separate from the probe. The probe and the local user interface device may each comprise wireless interfaces wherein the probe is configured to transmit the ultrasound image data to the local user interface device by way of the wireless data interfaces.

Some embodiments provide a camera operable to generate a video stream wherein the data interface is configured to transmit the video stream from the camera to the remote interface. The video stream and/or ultrasound image data may be buffered in corresponding image buffers. The ultrasound imaging device may be configured to receive a freeze message by way of the remote interface, the freeze message identifying a selected one of the plurality of frames of the video stream or the ultrasound image data, and, in response to the freeze message, to display on the display the selected one of the plurality of frames.

In some embodiments the ultrasound imaging device is configured to receive from the remote interface by way of the data interface one or more annotations and to display the one or more annotations on the display of the selected frame. The ultrasound imaging device may comprise a plurality of stored annotations wherein the ultrasound imaging device is configured to receive from the remote interface by way of the data interface an annotation message identifying a selected one of the stored annotations and, in response, to retrieve and display the selected annotation on the display of the selected frame.

In some embodiments the probe comprises a directional indicator such as a display or indicator lights and the ultrasound imaging device is configured to operate the directional indicator on the probe to indicate a position correction corresponding to one of the position correction messages.

Some embodiments comprise a demonstration device equipped with a position sensor in communication with the remote interface. In such embodiments the remote interface may be configured to transmit data comprising tracked positions and orientations of the demonstration device to the ultrasound imaging device and the ultrasound imaging device is configured to generate and display an animation corresponding to the tracked positions and orientations of the demonstration device.

Another aspect provides a remote interface having features as described herein.

The methods and systems described herein may increase the effectiveness of remote feedback, thus helping inexperienced ultrasound users to capture accurate images in less time, ultimately leading to improved patient care and reduced costs.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Acquiring an ultrasound image of a desired portion of a patient's anatomy is a challenging spatial-motor task. 2D ultrasound produces a 2D planar image. An operator must position a probe such that a 2D imaging plane is positioned in 3D space to capture a desired image. Capturing the desired image requires manipulating the probe to get the correct translation and rotation. Often, force must be applied to the patient so there is also compression. The mnemonic "PART" is often used to describe the different probe maneuvers: pressure, alignment, rotation, and tilt.

Like most manipulation tasks, it is possible to divide orienting the ultrasound probe into gross and fine movements. In the gross positioning phase, it is important to get the patient into an appropriate posture for the exam and place the probe at approximately the right location. Ultrasound images can then be acquired and used for preliminary feedback to gauge whether a different approach may be required.

Fine positioning typically involves numerous small movements to allow the operator to get a better idea of that particular patient's anatomy. As this is being done, the operator will use ultrasound images to guide what sort of rotation and translation is required to achieve the desired image. Once the desired scan plane is found, the operator will typically capture, or freeze that image for further analysis or documentation. A typical ultrasound exam may involve capturing images from several different scan planes.

Ultrasound scanning techniques are typically taught with reference to standard scanning planes and standard movements. For example standard scan planes are often described with reference to the coronal, transverse, and longitudinal planes of the patient's body. Translational movements of the probe may be described as sliding with respect to the patient's body, for example toward the head or toward the feet, toward the midline, etc. Rotation movements can also be described with reference to the patient's body or the probe itself.

Figure 9:
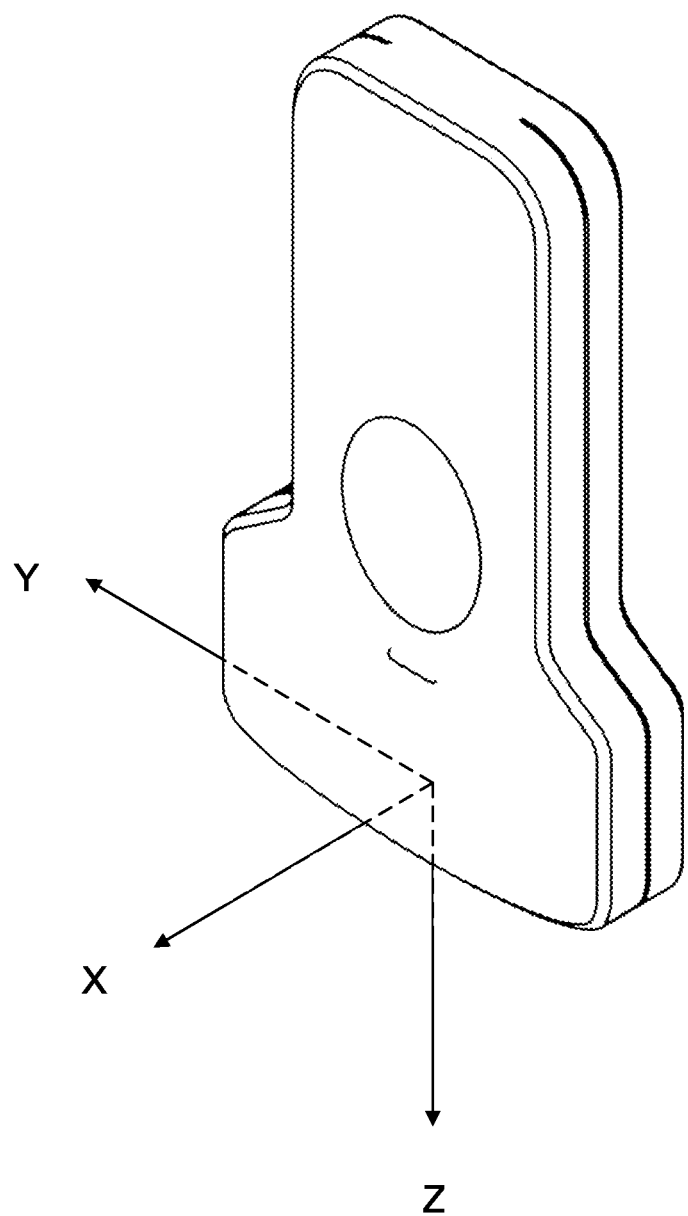
FIG. 9 is a diagram depicting an example coordinate system for an ultrasound probe.

FIG. 9 is a diagram of a typical ultrasound probe with a coordinate system. The origin of the coordinate system is centred on the face of the transducer. The z-axis is aligned with the long axis of the probe. The y-axis is parallel to the probe elements. The x-axis is mutually perpendicular to both the y- and z-axes. Movements and rotations of the ultrasound probe may be described with respect to this coordinate system.

Probe translation involves moving the probe in the XY plane. The different rotations of the probe can be described with respect to rotation around the different axes and are described as "rocking", "tilting", and "rotation".

Rocking, or heel-toe involves rotating the probe around the x-axis. This movement does not change the scan plane, but can be used to extend the field of view.

Tilting, or angulation involves rotating the probe around the y-axis. This movement sweeps through a volume and can be used to get a three dimensional impression of the anatomy or locate specific targets.

Rotation involves rotating around the z-axis. Rotation may be used in combination with sliding movements to trace a curved structure. Rotation may also be used alone to image a structure in different, often perpendicular, planes. For example, to image a vessel longitudinally and in cross-section.

An ultrasound system may provide features that allow a person at a remote site (e.g. an expert ultrasound user) to review the actions of a person using an ultrasound system and provide feedback. The feedback can help the user of the ultrasound system to learn proper operating techniques and can also help to ensure that images acquired by the user are of a suitable quality.

Example System

Figure 1:
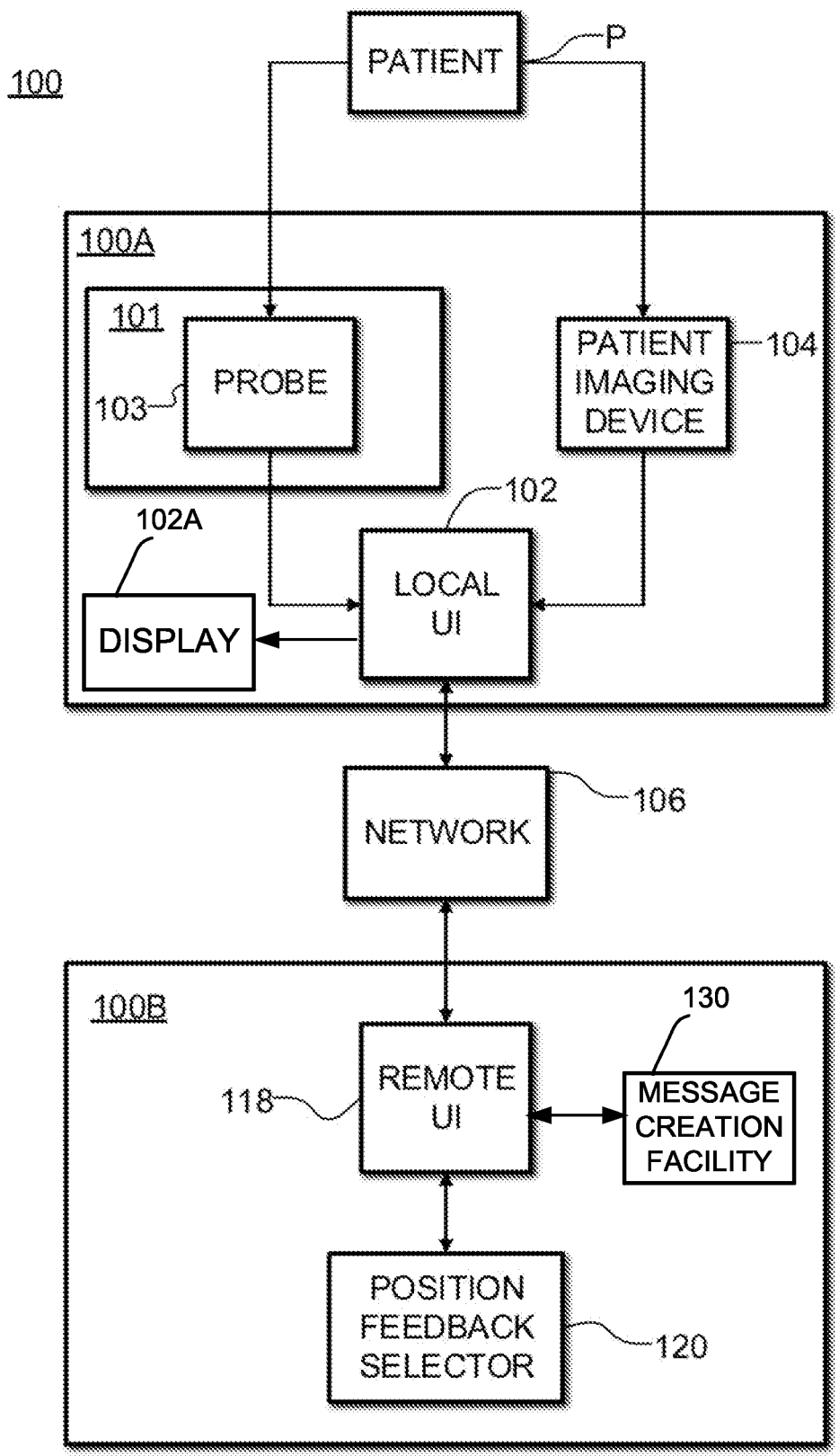
FIG. 1 is a schematic diagram of an ultrasound imaging system according to an example embodiment.

FIG. 1 is a schematic diagram of an example ultrasound imaging system 100 capable of providing remote feedback. System 100 comprises apparatus 100A at a location where a user performs an ultrasound scan on a patient and apparatus 100B at a remote location. An expert may use apparatus 100B to review information about an ultrasound procedure in real time as the ultrasound procedure is being performed at apparatus 100A and to provide real time feedback to a user of apparatus 100A.

The expert may, for example, use system 100 to provide feedback on how to capture a high quality image. This feedback may include adjustments to the type or amount of acoustic coupling used, gross positioning, fine positioning, or imaging parameters.

In the illustrated embodiment, an ultrasound imaging apparatus 101 transmits ultrasound waves into and receives ultrasound echoes from a patient P, which may be a human or an animal, for example. The ultrasound echoes are processed into ultrasound imaging data. The ultrasound imaging data is transferred to a local user interface device 102. Ultrasound imaging apparatus 101 comprises a hand-holdable probe 103 that may be scanned over a patient to acquire desired ultrasound images. It is convenient but not mandatory that electronics for generating ultrasound waves and receiving ultrasound echoes and performing at least some processing of the ultrasound echoes are contained within probe 103. In some embodiments ultrasound imaging apparatus 101 provides a self-contained battery-powered ultrasound image acquisition device that contains all circuitry required for obtaining ultrasound images and wirelessly transmitting the acquired ultrasound images to another device in real time. In alternative embodiments, ultrasound imaging apparatus 101 comprises some components not contained within probe 103.

Local interface 102 may include a user interface which includes controls for controlling aspects of the operation of ultrasound imaging apparatus 101. Device 102 may include a display on which images represented in the ultrasound imaging data from ultrasound imaging apparatus 101 may be displayed.

In some embodiments, local user interface device 102 is a general purpose device configured by software to operate as described herein. For example, local user interface device 102 may comprise a general purpose device such as a tablet computer, a smart phone, a laptop computer, a personal computer, a computer workstation or the like. In other embodiments local user interface device 102 comprises a custom electronic device.

Local user interface device 102 may be separate from ultrasound imaging apparatus 101 as illustrated or may be integrated with ultrasound imaging apparatus 101. Where ultrasound imaging apparatus 101 is separate from local user interface device 102, ultrasound imaging apparatus 101 may be in wireless data communication with local interface device 102. In other embodiments local interface device 102 and ultrasound imaging apparatus 101 are tethered by a suitable cable that provides a data communication path.

A patient imaging device 104 captures patient images showing probe 103 and patient P. The patient images may comprise a video stream. In some embodiments the patient images may comprise a sequence of still images. Imaging device 104 may, for example, comprise a suitable video camera, web camera, security camera or the like.

In some embodiments patient imaging device 104 is integrated with local user interface device 102. For example, where local user interface device 102 comprises a tablet, laptop or cellular telephone equipped with a camera, that camera may be configured to operate as patient imaging device 104. Patient imaging device 104 transmits the video stream to local user interface device 102. Local user interface device 102 may display the ultrasound imaging data and/or video stream from patient imaging device 104 to the operator on a display 102A.

A user of apparatus 100A may request remote assistance from an expert at apparatus 100B. For example, when a user is ready to begin imaging and requires assistance, they can activate a control on local interface device 102 (which may, for example, comprise a smartphone), to initiate a connection with a remote expert at remote apparatus 100B.

When remote feedback is desired apparatus 100A is caused to transmit one or both of the ultrasound imaging data and the video stream through a data communication network 106 to remote apparatus 100B. Apparatus 100A may send other data to apparatus 100B instead of or in addition to the video stream. Additional data may include positional measurements of probe 103, positional measurements of the patient, measurements of forces applied to the patient by probe 103, or a secondary video, for example.

The remote expert may provide feedback by interacting with a remote interface 118. In some embodiments remote interface 118 is a general purpose device configured by software to allow a remote expert to review an ultrasound procedure and provide feedback as described herein. For example, remote interface device 118 may comprise a smartphone, tablet, laptop, or personal computer configured by software to perform the functions of remote interface 118 as described herein. In other embodiments, remote interface 118 comprises a custom electronic device.

How the expert interacts with remote interface 118 will depend on the design and configuration of remote interface 118. In some embodiments, remote interface 118 comprises a touchscreen. For example, the remote expert may click or drag and drop an icon that corresponds to a desired feedback. The remote expert may drag and drop the icon onto the display of an ultrasound image stream or video stream at remote interface 118. In a preferred embodiment, the local user interface 102 is updated with the position of the icon in real time as the icon is applied by the expert.

Network 106 may comprise a local area network (LAN), wireless area network (WAN), cellular network, satellite communication, the Internet, dedicated wired or wireless or fiber optic connection, telephone line, cellular data connection, or the like, or some combination thereof. Any suitable data communications protocols may be used. In some embodiments each of local interface device 102 and remote interface 118 provide one or more TCP-IP type sockets for carrying data communications between apparatus 100A and apparatus 100B.

In the illustrated embodiment, local user interface device 102 is operable to transmit the ultrasound imaging data and the video stream data through data communication network 106 to remote apparatus 100B which includes remote interface 118. The remote expert can then use remote interface device 118 to view one or both of the ultrasound imaging data and the patient image data. This is preferably done in real time as a user is performing an ultrasound scan using probe 103. In some embodiments, patient imaging device 104 is adjustable (for example has adjustable pan and/or zoom) and remote interface device 118 includes controls that allow the expert to remotely adjust patient imaging device 104 to obtain a clear view of the procedure or a view that can best help the user to see and understand how to best conduct a scan. For example, the remote user may adjust pan and/or zoom of patient imaging device 104 and/or select video streams from different ones of a plurality of patient imaging devices 104 which are located to view the procedure from different points of view.

In some embodiments probe 103 includes a force transducer connected to monitor an amount of pressure (compression) being applied by the user to the patient. An output signal from the force transducer may be delivered to remote interface 118. Remote interface 118 may display an indication of the amount of pressure being applied for evaluation by an expert.

Position Feedback

If the remote expert considers that the user's technique for performing the ultrasound scan could be improved then the remote expert may provide feedback to the user by way of remote user interface 118. To achieve this, the expert may activate physical controls (such as buttons, joysticks, trackballs, switches, computer mice or the like); interact with a tough screen of remote interface 118; issue voice commands; use a stylus or other pointing device to operate controls presented by a graphical user interface of remote interface 118 or the like. In some embodiments remote interface 118 includes a demonstration device which can be positioned like probe 103 and is equipped with a position sensor. The demonstration device may be a probe 103 or a replica of probe 103 for example. The expert may manipulate the demonstration device to demonstrate a particular technique while the position and orientation of the demonstration device is tracked. The tracked position and orientation of the demonstration device may be transmitted to apparatus 100A which may generate an animation showing the user of apparatus 100A how the expert is manipulating the demonstration device.

Figure 3:
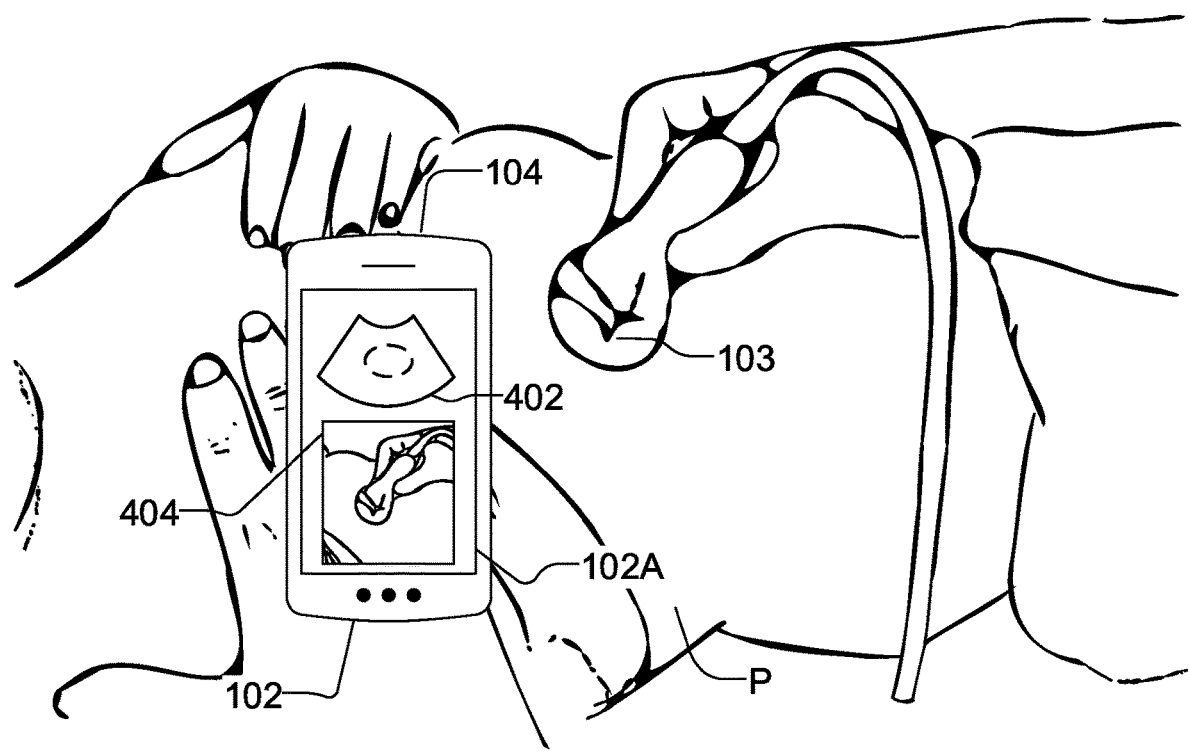
FIG. 3 is a diagram showing a patient and an example local user interface device.

FIG. 3 is a diagram showing an example of a local user interface device 102. The operator is holding probe 103 against the abdomen of patient P. In this case, patient image device 104 comprises a digital camera integrated into local user interface device 102. An ultrasound image 402 captured by probe 103 and a video stream 404 captured by camera 104 are displayed simultaneously on display 102A of local user interface device 102.

Figure 4:
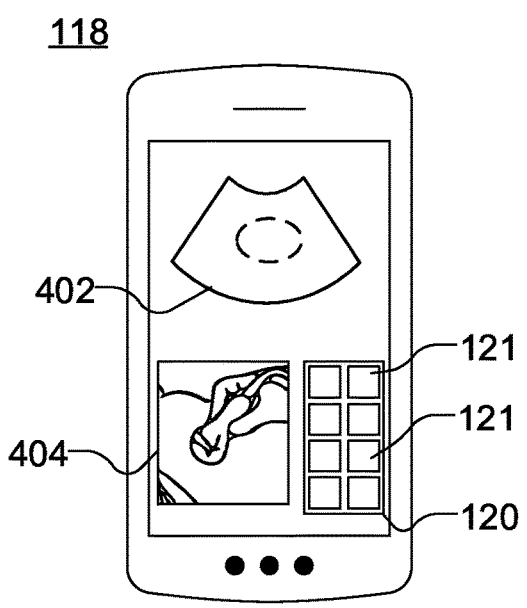
FIG. 4 is an example of a remote user interface device.

FIG. 4 is an example of a graphical display that may be produced at a remote interface device 118. The display includes ultrasound image 402 and video stream 404 as well as controls that may be used by an expert to provide direction and feedback to a user.

FIG. 4 includes a plurality of graphical feedback elements 121 for selection by an expert. These feedback elements may be actuated by the expert to generate predetermined messages.

Figure 5A:
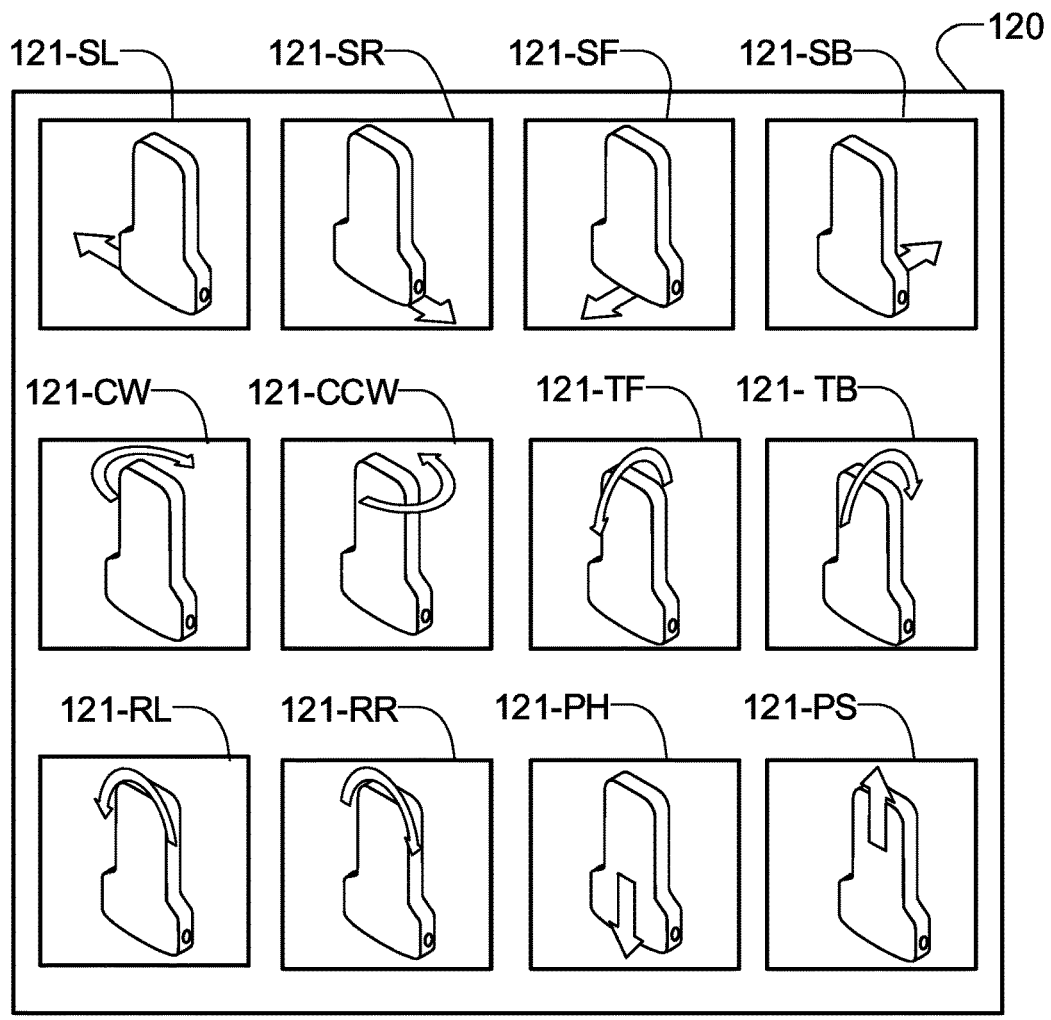
FIG. 5A is an example of graphical controls displayed in a positional feedback selector.

In some embodiments some or all of the feedback is in the form of discrete messages. These discrete messages may be selected from a set of predetermined discrete messages. The predetermined messages can include messages to change the position of probe 103. In the illustrated embodiment, remote interface 118 includes a position feedback selector 120 configured to allow a remote expert to trigger remote interface 118 to send selected discrete messages to apparatus 100A. In a preferred embodiment the discrete messages include messages signifying:

move probe 103 to the left;
move probe 103 to the right;
move probe 103 toward the front;
move probe 103 toward the back;
rotate probe 103 clockwise;
rotate probe 103 counterclockwise;
tilt probe 103 forward;
tilt probe 103 backward;
rock probe 103 to the right;
rock probe 103 to the left;

FIG. 5A shows an example feedback selector 120. In the illustrated embodiment, feedback selector 120 has the form of a palette comprising several individual controls 121. Controls 121-SL, 121-SR, 121-SF, and 121-SB respectively trigger messages for moving (sliding) probe 103 to the left, to the right forward and backward; controls 121-CW and 121-CCW respectively trigger messages for rotating probe 103 clockwise and counterclockwise; controls 121-TF and 121-TB respectively trigger messages for tilting probe 103 forward and backward; and controls 121-RR and 121-RL respectively trigger messages for rocking probe 103 to the right and to the left.

In some embodiments the predefined discrete messages include messages signifying increase pressure on probe 103 and decrease pressure on probe 103. In the illustrated embodiment, feedback selector includes controls 121-PH and 121-PS which respectively trigger messages indicating that the user should push probe 103 harder (increase compression) or more softly (decrease compression) against the patient.

Figure 5B:
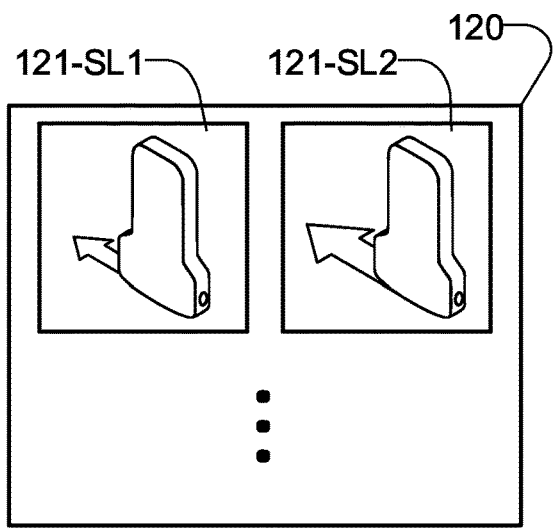
FIG. 5B is an example of an alternative embodiment of graphical controls.

In some embodiments feedback selector 120 includes controls that cause the messages to indicate a degree of required movement (i.e. controls that allow the expert to indicate that the suggested movement should be a relatively small movement or a relatively larger movement). There are a number of ways to implement such controls. One way is to include in feedback selector 120 duplicate sets of controls 121 corresponding to different sizes of motions. For example, each of the above-noted controls 121 could comprise a pair of controls, one corresponding to messages indicating a smaller motion and one corresponding to messages indicating a larger motion. An example of this is shown in FIG. 5B.

As another example (not shown), controls 121 could each comprise a triplet of controls with one control arranged to trigger a message indicating a small motion, another control arranged to trigger a message indicating a medium motion and a third control arranged to trigger a message indicating a large motion. This same principle may be extended to any reasonable number of controls.

Figure 5C:
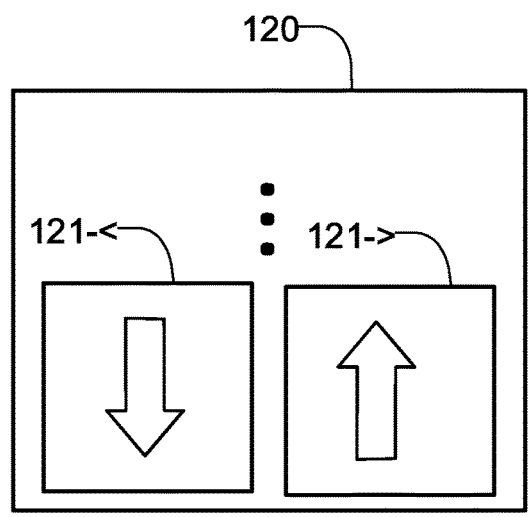
FIG. 5C is another example of an alternative embodiment of positional graphical controls.

In another example shown in FIG. 5C feedback selector 120 includes one or more separate controls for indicating a magnitude of suggested motion. In the illustrated embodiment controls 121-< and 121-> are provided. With this arrangement an expert can trigger a message for a suggested movement as described above. In addition the expert may optionally operate control 121-< and then the control 121 for the desired movement to signify that the movement should be small or operate control 121-> and then the control 121 for the desired movement to indicate that the movement should be large. In an alternative embodiment (not shown), feedback selector 120 may include + and − controls that can be actuated one or more times to respectively command transmission of messages indicating progressively larger or progressively smaller magnitudes of motion.

Remote interface 118 may additionally or in the alternative include a gesture-based feedback selector. For example, messages indicating motions to the right or left could respectively be triggered by swipes to the right and left; messages indicating clockwise or counterclockwise rotations could respectively be triggered by two-finger gestures in which the fingers move clockwise or counterclockwise relative to one another; messages indicating tilts could respectively be triggered by downward and upward swipes respectively.

Whatever mechanism is used by the expert at remote interface 118 to select messages for transmission to the user, the selected feedback is transmitted back through network 106 to local user interface device 102 and displayed to the user. Advantageously, a predetermined set of messages may be stored at interface device 102 such that the communication from remote interface 118 needs only to identify the message to be displayed to the user. In such embodiments the message content does not need to be transmitted. Each message may, for example, be represented by a number or other small message ID code. Upon receiving from remote interface 118 an indication that a predetermined message should be displayed, interface device 102 may retrieve and display the predetermined message.

Preferably, each message corresponding to a desired movement comprises an arrow indicating the direction and type of the desired movement such that a user can immediately and intuitively see what type of movement is being suggested by the remote expert. For example, each predetermined message may correspond to a predetermined icon that can be displayed on display 102A. In some embodiments the icons comprise semi-3D or isometric icons depicting probe 103 which include arrows to indicate the desired motion with rotation, tilting or pressing arrows.

Figure 5D:
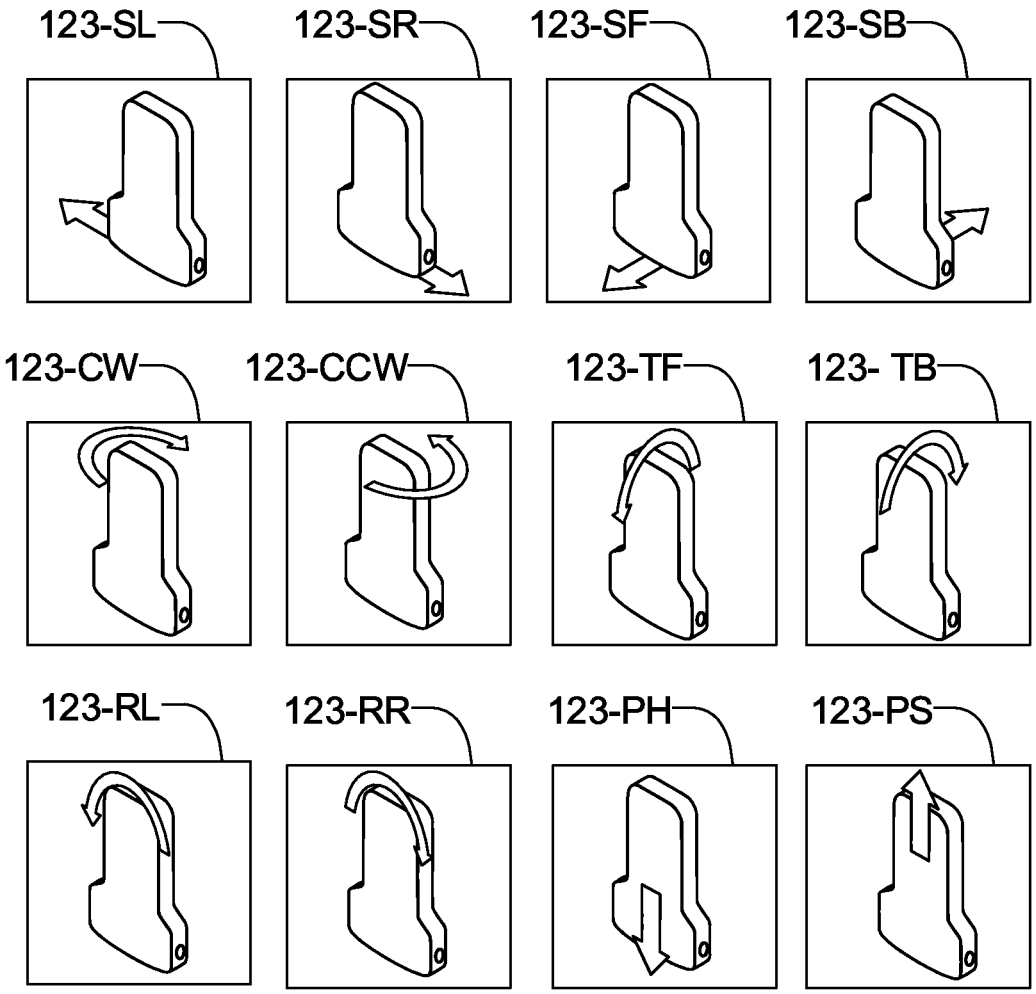
FIG. 5D is an example of graphical feedback icons.

FIG. 5D shows non-limiting examples of icons 123 that may be displayed at interface device 102 to deliver predetermined messages to a user of apparatus 100A. Icons 123 include icons 123-L and 123-R for respectively signalling movements to left and right; icons 123-CW and 123-CCW for respectively signalling clockwise and counterclockwise rotations; and icons 123-F and 123-B for respectively signalling tilt forward and tilt backward. In embodiments which support indications of the suggested magnitude of movements, the sizes of arrows in icons 123 may be increased and/or decreased to indicate larger or smaller movements.

Ideally the icons indicating messages from the expert are relatively large so that they can be immediately seen and understood by a user. Ideally the icons are displayed at the top of display 102A.

Message Persistence

Messages from the expert may have a controlled persistence. For example, an icon or other visual depiction of a message from remote interface 118 may be automatically deleted or faded a predetermined time after it is received at local user interface 102. In some embodiments, each icon fades after a few seconds or when a new message for display is received from remote interface 118, whichever is first.

In some embodiments apparatus 100B fades or discontinues displaying messages in response to determining that the message has been acted on. For example, a message suggesting a particular movement may persist only until the suggested movement is detected (e.g. based on a signal indicating movements of probe 103). Such signals may be generated in any of the ways discussed elsewhere herein.

In some embodiments display of messages at apparatus 100A can be discontinued by a control signal from apparatus 100B. For example, an expert may send a message indicating satisfaction with the current state of the ultrasound exam. In response to receiving that message the display of previous messages may be discontinued.

In some embodiments an expert may indicate a combination of motions (e.g. by selecting two controls 121). In such cases apparatus 100A may alternate displaying messages (e.g. icons) for the two motions or display a composite icon that includes arrows showing both motions.

Feedback Delivered by Way of Probe

Figure 10A:
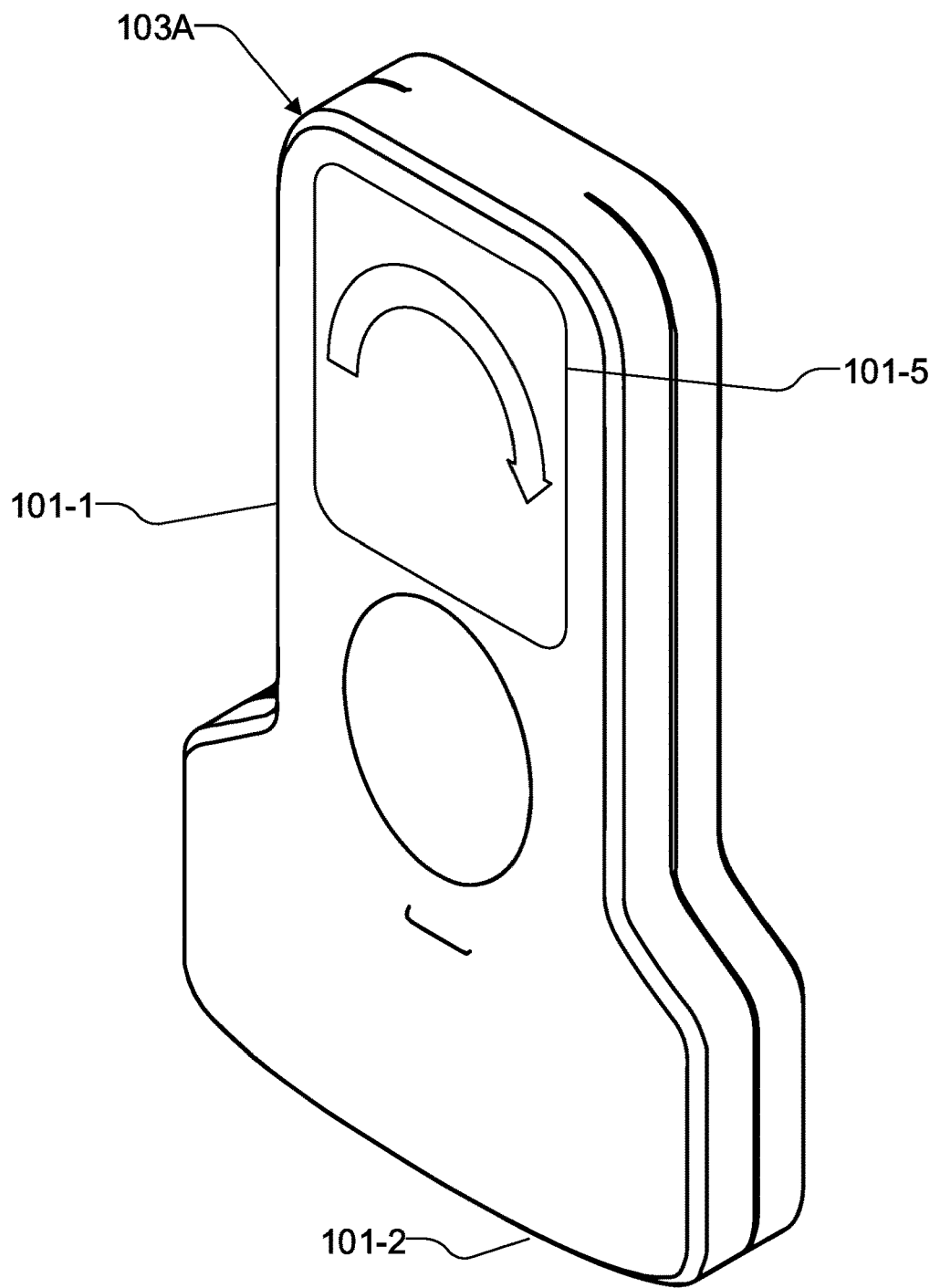
FIG. 10A is an alternative embodiment of the probe with an integrated display.
Figure 10B:
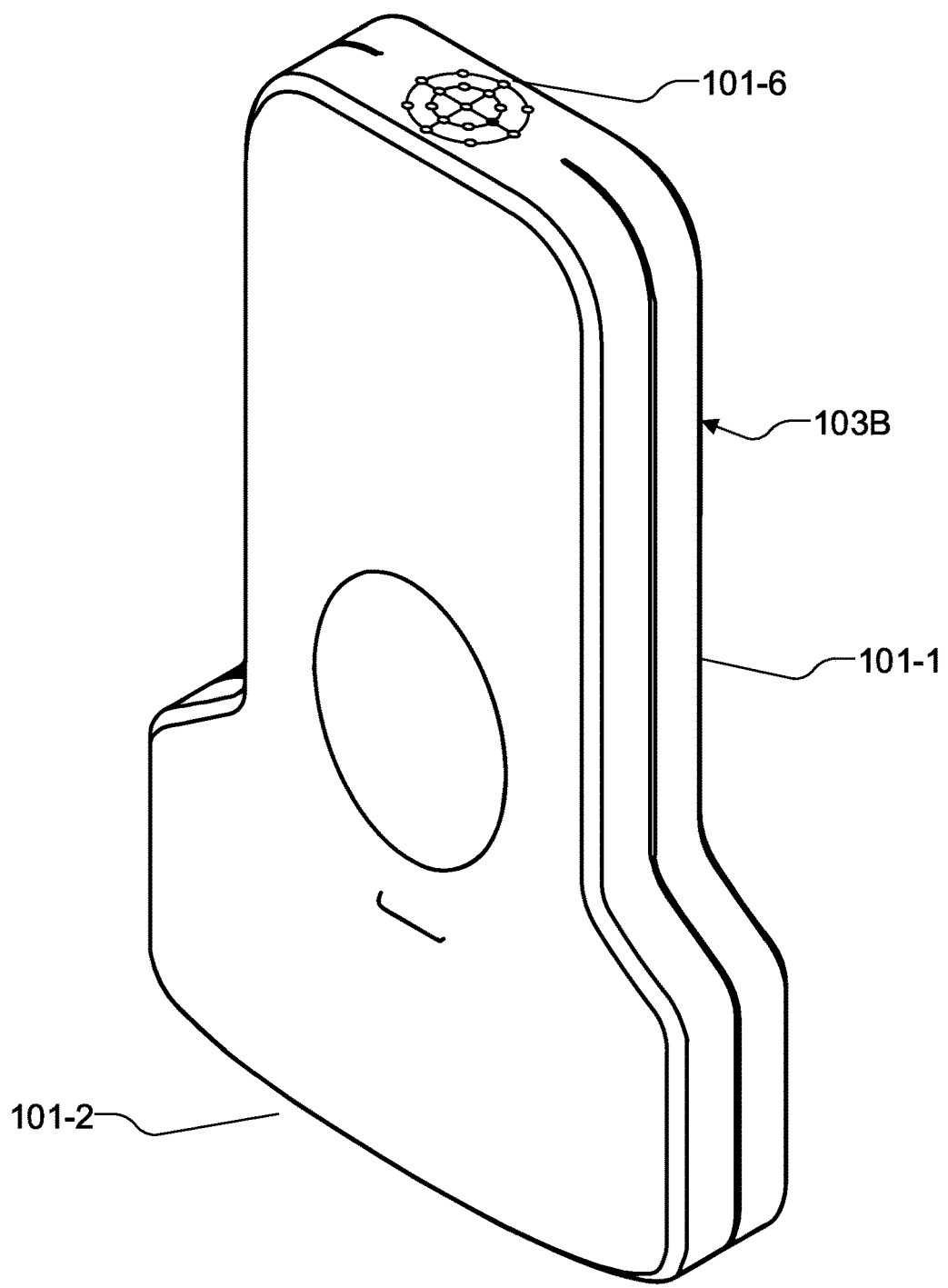
FIG. 10B is another alternative embodiment of the probe with integrated feedback elements.

In addition to or as an alternative to displaying messages, e.g. on display 102A, messages may trigger indications on probe 103. For example, probe 103 may include a small display and/or LED lamps which are controlled in predetermined ways in response to messages received from remote interface 118. FIGS. 10A and 10B provide example probes 103A and 103B. Each of these probes includes a hand-holdable body 101-1 having an ultrasound transducer 101-2 at one end. Electronics for controlling the transducer to emit and receive ultrasound signals are contained within body 101-1.

Probe 103A comprises a small display 101-5 which is located where it can be seen by a user who is holding body 101-1 to perform an ultrasound scan. Display 101-5 may display predetermined static or moving images indicating motions corresponding to messages received from remote interface 118.

Probe 103B comprises an array of small lights 101-6 that are located where they can be seen by a user who is holding body 101-1 to perform an ultrasound scan. Selected lights 101-6 may be turned on to provide static or dynamically varying patterns selected to indicate motions corresponding to messages received from remote interface 118. For example, lights 101-6 on the left side of probe 103B may be controlled to blink to indicate motion to the left; lights 101-6 on the right side of probe 103B may be controlled to blink to indicate motion to the right; lights 101-6 on the front side of probe 103B may be controlled to blink to indicate forward tilt; lights 101-6 on the back side of probe 103B may be controlled to blink to indicate backward tilt; lights 101-6 may be controlled in a clockwise rotating pattern to indicate clockwise rotation; and lights 101-6 may be controlled in a counterclockwise rotating pattern to indicate counterclockwise rotation. Lights 101-6 may be controlled to indicate increased or decreased applied pressure, for example by changing the color of lights 101-6 or pulsing lights 101-6 in a characteristic way.

Monitoring User Responses

In addition to merely displaying messages to a user at apparatus 100A, system 100 may include functions for monitoring to determine whether or not a user is correctly following the suggestions conveyed by the messages. In some embodiments such monitoring comprises one or more of:

monitoring changes in received echo signals and/or the ultrasound imaging data to detect motions of probe 103 relative to the patient;

providing an accelerometer in probe 103 and monitoring one or more outputs of the accelerometer to detect and/or measure inclination of and/or rotations of the probe 103;

providing a position sensor in probe 103. The position sensor may, for example, be of the general type used to sense motions of a ball-type or optical computer mouse and may be located to sense motions of probe 103 over the surface of a patient.

If the monitored motion does not correspond to the message received from remote interface 118 then a warning signal may be provided to the user. The warning signal may, for example, comprise a sound, tactile feedback or the like. For example, probe 103 may be controlled to deliver a vibration or other haptic feedback to a user if the user moves the probe 103 in the wrong way. As another example, a display of apparatus 100A (e.g. display 102A) may be controlled to display a 3D rendering of probe 103. The display may be, for example in a corner of the screen. The rendering may change colour if the system detects that the probe 103 is not aligned properly.

It is not mandatory that messages be delivered visually at apparatus 100A. In the alternative, or in addition, messages may be delivered by other means. For example by one or more of:

audio messages may be provided. In some embodiments the audio messages may include synthesized or pre-recorded speech messages such as 'scan left'; 'scan right'; 'tilt forward' etc. Such audio messages may optionally be delivered privately to a user, for example by way of an earpiece. In some embodiments the earpiece communicates wirelessly (e.g. by Bluetooth™) with local user interface 102. Such messages may be delivered in a language corresponding to a language setting for local user interface 102. In such embodiments it is not necessary for the expert to speak or understand the language in which the messages are delivered to the user;

text messages may be displayed on a display of apparatus 101A, for example on screen 102A. The text messages may include predetermined statements such as such as 'scan left'; 'scan right'; 'tilt forward' etc. The text messages may be delivered in a language corresponding to a language setting for local user interface 102;

tactile feedback may be provided. In some embodiments the tactile feedback is provided by transducers such as piezoelectric transducers and/or heaters on a housing of probe 103 that may be selectively actuated to change the texture, temperature and/or vibration patterns sensed by a user holding probe 103 in a manner that maps intuitively to suggested movements.

Other Messages

The predetermined messages that remote interface 118 is configured to deliver may include messages that communicate other suggestions to the user. Such predetermined messages may be selected to cover a range of issues that typically arise when inexperienced users are operating ultrasound equipment. To keep remote interface 118 relatively uncluttered, different sets of additional predetermined messages may be provided for different types of ultrasound procedures and only those predetermined messages relevant to a current procedure may be displayed for selection by the expert at remote interface 118. Examples of possible predetermined messages include:

Unacceptable;
Acceptable;
Start again;
Move on to capture the next image in this series;
Reposition the patient (in a specified way);
Apply more gel to the transducer;
Change the ultrasound settings (in a specified way);
Good job;
Move camera to better show patient;
etc.

Such additional predetermined messages may be delivered in any of the manners described above. Remote interface 118 may comprise a menu from which an expert may select additional messages to deliver to a user. The messages may be delivered in real time.

Predetermined messages may result in various types of display at apparatus 100A. For example, a certain predetermined message may display as an icon having the desired significance. In the alternative, predetermined messages may be presented as text in a certain area.

In addition to one or more other kinds of feedback, local interface device 102 and remote user interface 118 may optionally be configured to support two-way voice communication between the user of apparatus 100A and the expert at apparatus 100B.

Rapid Custom Messages

In some embodiments, remote interface 118 includes a facility 130 which permits the expert to rapidly create customized messages which indicate an action for the user of ultrasound imaging apparatus 101 to perform. Facility 130 may use the video stream from patient imaging device 104 as a basis for some such messages.

Freeze Frame

In one example, the expert may operate a control that selects a frame of the video stream to freeze. The expert may then annotate the frozen frame. Selecting a frame to freeze may be done in real time, for example, by actuating a control when a desired frame is being shown. In another embodiment an expert may replay a portion of a video or ultrasound data stream that is buffered at remote user interface 118. The replay may be done forward or backward at original speed or a faster or slower speed or a speed controlled by the expert. The expert may go back and forth through the buffered frames until a suitable frame is identified. The expert may then operate a control to use the selected frame as the basis for a message to the user.

For example the expert may annotate the frozen frame to show a desired change in position and/or orientation of probe 103. In an example embodiment this is done by indicating starting and ending positions or orientations of the probe 103.

In some embodiments, remote interface 118 provides a freeze control that causes a current frame of the video stream to be frozen. Remote interface 118 may automatically generate and send to apparatus 100A a freeze message containing an identifier of the frozen frame (e.g. a frame number). Upon receipt of the freeze message apparatus 100A may retrieve the selected frame and display it instead of or in addition to the video stream (e.g. on display 102A). Display of the ultrasound image data may be frozen in a similar way. At apparatus 100A frozen video or ultrasound image data may be displayed in a characteristic manner that identifies it as being frozen under control of remote interface 118. For example, the frozen image may be displayed together with a particular icon or symbol or overlaid with a particular color or the like.

One way in which the starting and ending positions may be input is for the expert to position or position and orient an icon representing probe 103 at a starting position on the frozen frame. The starting position may, for example be the location at which the probe 103 is shown in the frozen frame. The expert may then position or position and orient an icon representing probe 103 at a desired position in the frozen frame. The expert may then operate a control to cause remote interface 118 to send the message.

Since the video stream originated at apparatus 100A it is not necessary to send the frozen frame to apparatus 100A. Remote interface 118 may be configured to generate a message that indicates which frame of the video stream was frozen by the expert and the starting and ending positions (or positions and orientations). At apparatus 100A (for example at local user interface 102) the message is received and processed. Processing the message may comprise retrieving from a data store and displaying the indicated frame of the video stream, and displaying icons on the frame at the starting and ending positions/orientations. In some embodiments, processing the message comprises generating an animation illustrating movement of the probe 103 from the starting to the ending position. Such an animation may assist the user to see how to reposition the probe 103 for better results.

The remote expert may use a freeze frame control to provide feedback to indicate a desired view while the probe is in motion. This feature may be implemented as a remote freeze, enabling the expert to remotely indicate the desired view. For example, the remote expert could instruct the local user to slowly rotate the probe. The remote expert would then actuate a freeze control on remote interface 118 when the probe is capturing the desired image. The freeze control may optionally freeze both the ultrasound image data and the video stream from patient imaging device 104. This way the user of apparatus 100A can see both what the ultrasound image should look like and the correct position and orientation for probe 103 to acquire the image.

To facilitate learning, the remotely frozen image may be used to help the local user realign to the desired scanning location. The frozen image may be used as a reference image so that the local user can re-align the probe to same position as when the remote expert indicated. For example, the frozen reference image could be displayed adjacent to the live ultrasound image, or overlaid with a transparency on display 102A so that the local user can try to adjust the position of probe 103 to match.

Additional information may also be captured when the remote expert remotely indicates a reference position (e.g. by operating a 'freeze' control). For example, the position of the probe and/or patient as measured by position sensors may be recorded. The recorded position information may be compared to current information on the position of the probe 103 and/or the patient. The result of the comparison could be used to provide additional feedback to help the local user align probe 103 with the desired position.

Highlighting

As another example, the expert may use remote interface 118 to highlight a particular area of an ultrasound image or a particular area within the video stream from patient imaging device 104. Highlighting may be performed on 'live' images or on a selected frozen frame of the ultrasound image data or the video stream. In an example embodiment highlighting is done using controls provided on remote interface 118 to identify the location that should be highlighted. Such highlighting may be done in any of a wide number of ways. For example, the expert may select a highlight control and position the highlight control at a desired location on the ultrasound image data being displayed on remote interface 118 (e.g. the interface may facilitate dragging and dropping a highlight control at a location to be highlighted). Selection and positioning the control may be done using a touch interface, a pointing device such as a trackball or stylus, or in any other suitable manner. The control may optionally permit the expert to select attributes (e.g. color, size, shape, orientation) for the highlighted region. Remote interface 118 may optionally be configured to allow the expert to optionally enter or select text to be displayed in conjunction with the highlighting.

Upon remote interface 118 detecting that the expert has selected a region to highlight, remote interface 118 generates a highlight message to apparatus 100A. Since the ultrasound images are available at apparatus 100A the highlight message does not need to include the ultrasound image but may be a short message containing coordinates for the highlighted region as well as any attributes of the highlighting (e.g. color or size for the highlighted region, any text to be displayed in conjunction with the highlighting).

Upon receiving a highlight message, apparatus 100A highlights the displayed ultrasound image (e.g. on display 102) at the coordinates indicated in the highlight message using the attributes, if any, provided in the highlight message.

Image Annotation

Some embodiments provide an annotation feature that may be used by an expert to annotate images (e.g. frames from the ultrasound imaging data generated by ultrasound imaging apparatus 101 and/or the video stream from patient imaging device 104). The annotations may be predetermined. For example, remote interface 118 may include a set of annotations depicting things that may be seen in an ultrasound image. The expert may arrange such annotations on an image to identify various features to the user. The predetermined annotations may include annotations like: "liver"; "lung"; "heart"; "kidney"; "bowel"; "blood vessel"; "urethra". Since the image data is already available at apparatus 100A the annotations may be communicated from apparatus 100B as short annotation messages identifying which frame of which source is to be annotated, which annotation is to be displayed and where are the coordinates at which the annotation is to be displayed. In some embodiments remote interface 118 is configured to allow the expert to select predetermined annotations from a set of predetermined annotations and to drag and drop the selected annotations at desired locations on a frozen image. This action may automatically generate annotation messages which may be used by apparatus 100A to create an annotated version of the same image for viewing by the user.

As with messages of other types, apparatus 100A may include a set of predetermined annotations in a language that is different from that used at remote interface 118. In some embodiments, apparatus 100A includes several sets of predetermined messages and/or annotations with each set in a different language. A user of apparatus 100A may select the desired language. For example, a Spanish-speaking expert may drag and drop an annotation reading "corazón" to indicate a portion of a frozen ultrasound image corresponding to a patient's heart. This predetermined annotation may have a particular reference number in system 100 such as "A2348". In response to this drag and drop operation, apparatus 100B may generate an annotation message having the content "A2348; F22365; X; Y" where F22365 indicates the particular frame of the ultrasound image data annotated by the expert X and Y are the coordinates at which the expert dropped the annotation. Apparatus 100A may be set to the English language. On receiving the annotation message, apparatus 100A may retrieve and display frame F22365 and retrieve annotation No. A2348 (which is an English-language annotation reading "heart") and place the annotation at location X, Y on the frozen image for viewing by the user.

In some embodiments the expert may also select annotations which can accept arbitrary text supplied by the expert.

In some embodiments the remote expert may add graphical elements to an image. These graphical elements may be provided to the user of apparatus 100A in a substantially real-time screen sharing mode. The graphical elements may include arrows, circles, or other shapes to indicate a point or region of interest.

Figure 6:
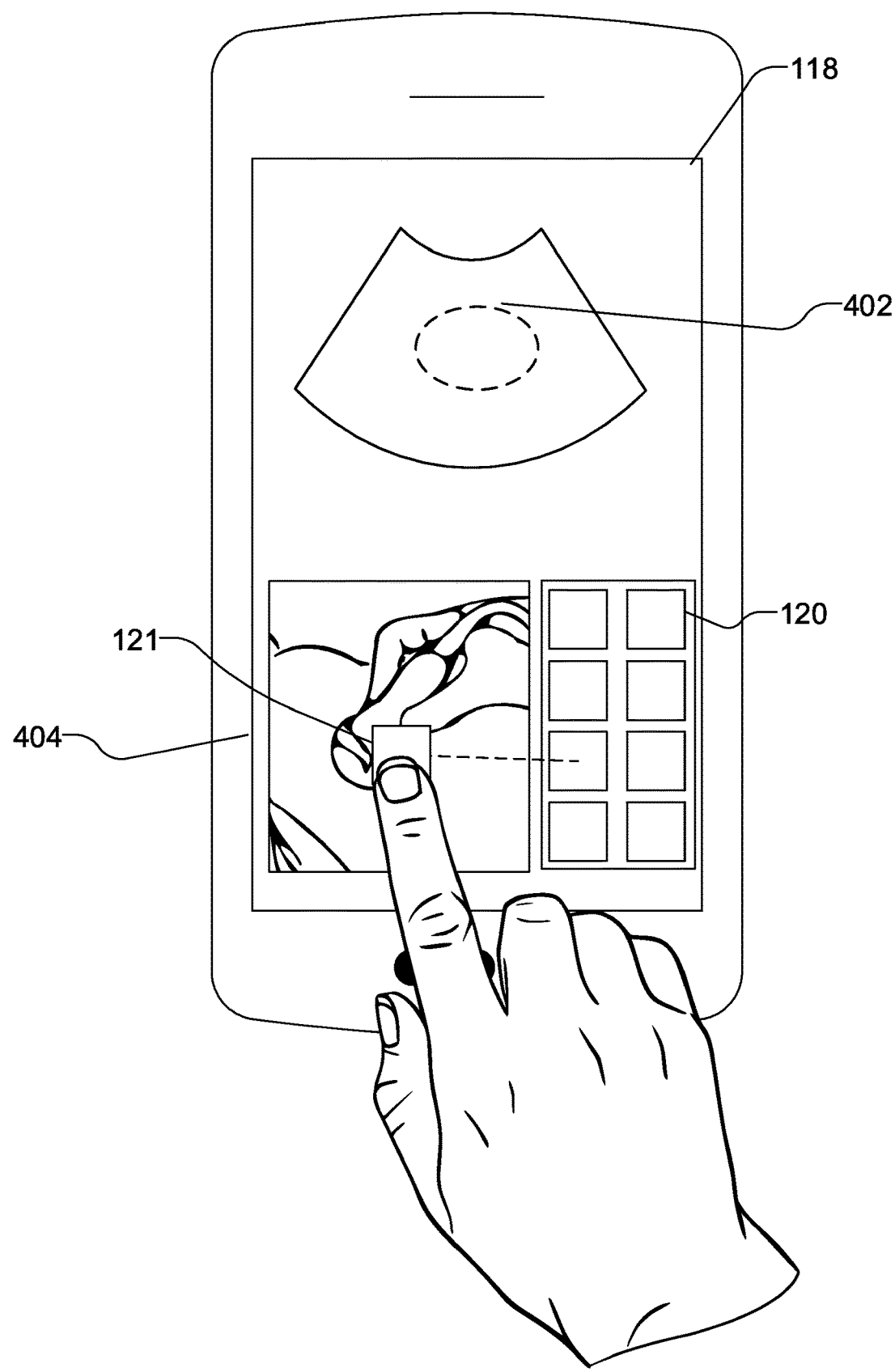
FIG. 6 is an example of a gesture that may be used to provide remote feedback.

FIG. 6 shows an example remote user interface with drag and drop graphical elements that a remote user can select to provide feedback. In the example, the expert drags and drops a targeting icon 121 onto patient video stream 404 to indicate the desired location of the probe. In some embodiments remote interface 118 sends a plurality of messages for a drag and drop event so that a user at apparatus 100A sees where the expert has dragged the icon in real time while the icon is being dragged by the expert at remote interface 118.

Optional Position Sensors and Applications

Figure 8:
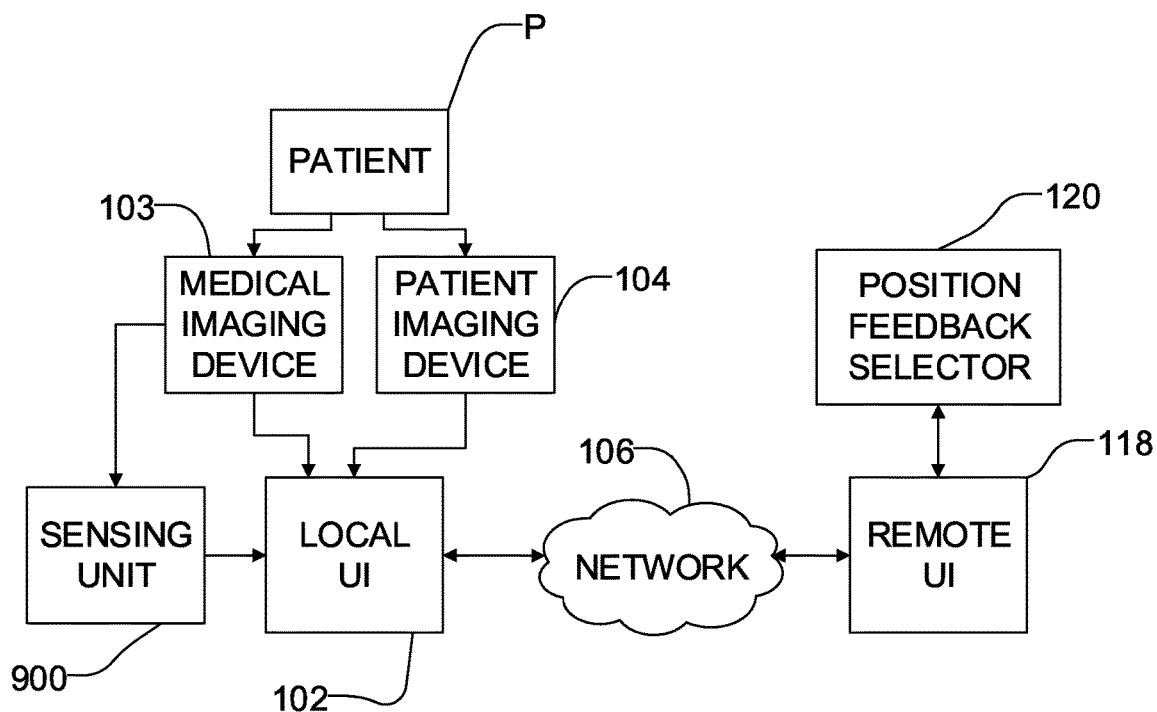
FIG. 8 is a schematic diagram of an ultrasound system according to another embodiment.

FIG. 8 is a schematic diagram illustrating an alternative version of apparatus 100A. In this embodiment, a sensing unit 900 is in communication with local user interface device 102. Sensing unit 900 is operable to measure the position, orientation, or both, of probe 103. Sensing unit 900 may comprise one or more sensors integrated into probe 103 such as one or more accelerometers, gyroscopes, or the like. In other embodiments, sensing unit 900 comprises tracking devices that monitor positions of probe 103 relative to one or more external references. Examples of such devices are optical trackers (some of which are configured to monitor positions of fiducial markers on probe 103 and others which are marker-less optical systems).

Sensing unit 900 is configured to provide device position information that indicates the position and orientation of probe 103. The device position information may be measured with respect to patient P, patient imaging device 104, local user interface device 102, or a different world reference. The device position information from sensing unit 900 may be applied for various purposes including:

Providing information to the expert regarding things such as the speed at which a user is moving probe 103 or the amount by which a user has changed an orientation of the probe 103 relative to one or more axes;

Permitting apparatus 100A to monitor whether or not a user is positioning the probe 103 as suggested in a message received from remote interface 118;

Automatically controlling patient imaging device 104 to follow motion of probe 103 (e.g. where patient imaging device 104 has a pan functionality).

Where apparatus 100A includes a sensing unit 900 it is meaningful for the expert to make more specific suggestions (e.g. tilt by about 12 degrees, slide right by 1.3 cm) because apparatus 100A can provide feedback to the user regarding when the specific movement has been achieved based on the device position information from sensing unit 900. In some embodiments apparatus 100A provides a display which depicts both a current position and orientation of the probe 103 and a new position as suggested in a message from remote interface 118. The user can see on the display when he or she has achieved the suggested position. Various cues may be given when the suggested position is reached or has nearly been reached. These cues may include audio cues, visual cues (e.g. green highlighting on the display), tactile cues (e.g. a pulse or vibration generated at an actuator in probe 103) or combinations of these, for example.

In some embodiments, apparatus 100A provides a sensor system configured to monitor a position of a patient (or a part of the patient being examined). In such cases the apparatus may track the position of probe 103 relative to the patient.

Measurement Assistance

Some ultrasound procedures require technicians to make measurements of anatomical structures. In such cases the technician must first obtain a good image of the structure to be measured from an appropriate angle. An expert can assist the user to obtain a suitable image as discussed elsewhere in this disclosure.

After a suitable ultrasound image has been obtained, the technician must identify the anatomical structure to be measured, select an appropriate measurement tool (in cases where more than one measurement tool is provided) and then define endpoints of the measurement that are located at the right places for the desired measurement. System 100 may be configured to facilitate training a technician to make such measurements or to assist an inexperienced user to achieve acceptable measurements.

The remote expert may provide assistance in making measurements on the image. The remote expert may fine-tune or adjust a measurement made by the local user or add additional measurements.

In some embodiments apparatus 100A includes a measurement tool comprising endpoints that a user can place at desired locations in an ultrasound image to perform a measurement. Apparatus 100A may automatically transmit the endpoints to apparatus 100B. Remote interface 118 may display the endpoints as set by the user of apparatus 100A.

Remote interface 118 may be configured to allow the expert to perform a measurement on the same ultrasound image. The expert may select a measurement tool, adjust the positions of endpoints provided by the measurement tool and take a measurement. Remote interface 118 may generate a message to apparatus 100A which identifies the measurement tool and endpoint locations. Apparatus 100A may display the expert's measurement (e.g. on display 102A). The expert's measurement and the user's measurements may be displayed in contrasting colors at each of apparatus 100A and 100B so that they can be readily distinguished.

In an alternative embodiment a measurement tool provided at apparatus 100A is configured to accept remote inputs from remote interface 118. In such embodiments the expert may be empowered to select particular measurement and/or adjust end points of the measurement, and indicate they are satisfied with the correction. Such changes may be reflected in real time at display 102A. In some embodiments the endpoints selected by the user may be preserved so that they can be compared to the endpoints selected by the expert.

Example Process

Figure 2:
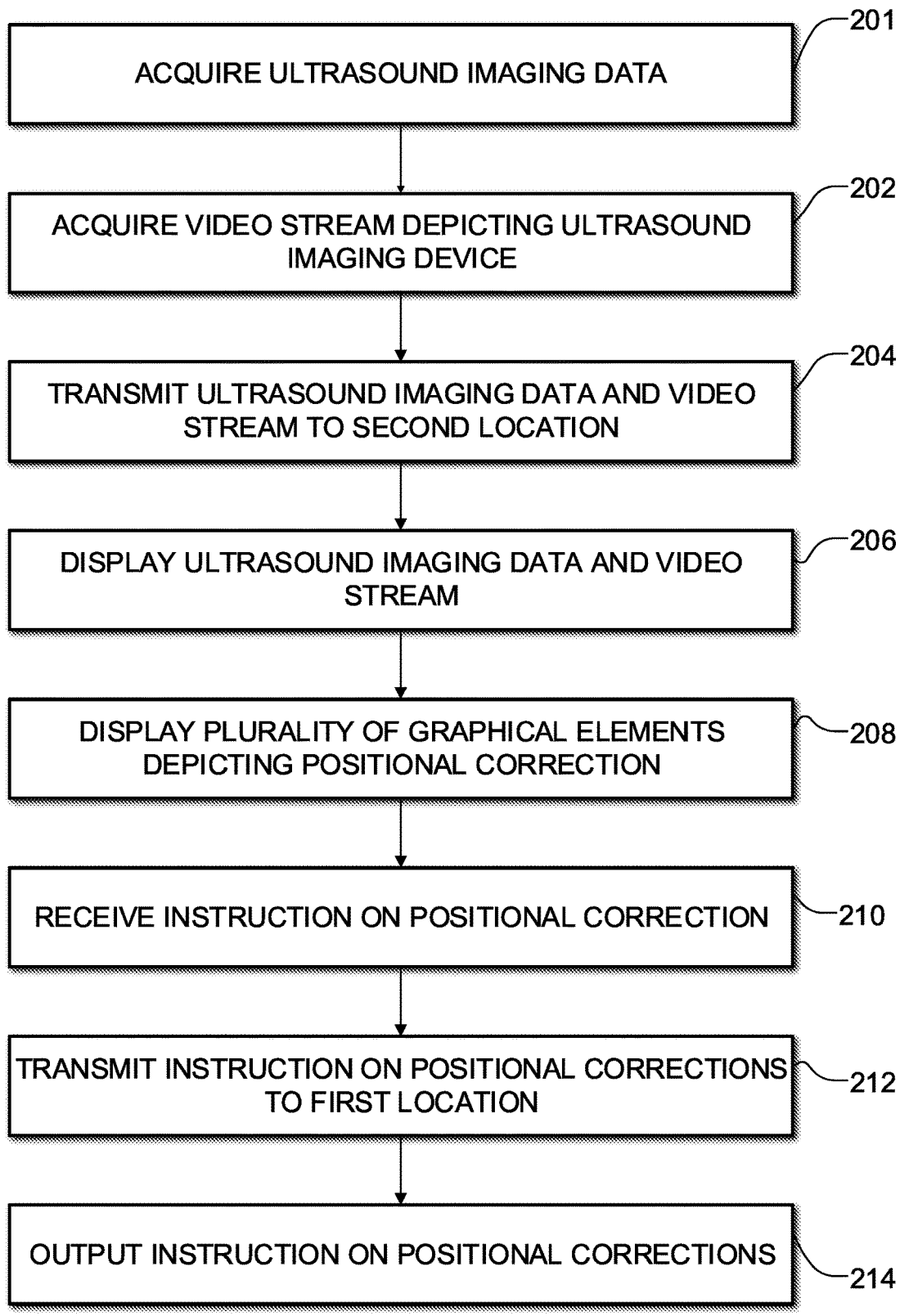
FIG. 2 is a process diagram illustrating an operation of an example ultrasound imaging system.

FIG. 2 is a process diagram illustrating an example method 200 which may be performed by an ultrasound imaging system. In operation 201, ultrasound imaging data is acquired. The operator places a probe against the patient. The probe generates ultrasound waves which travel into and are partially reflected back from the patient. The echoed ultrasound waves are measured by the probe and converted into ultrasound imaging data.

In operation 202, a video stream depicting the probe is acquired. Operations 201 and 202 may occur simultaneously. Preferably, the video stream depicts the probe in relation to the patient. The video stream may be captured by a camera. The camera may be attached or integrated with the probe, or the local user interface device, or may be mounted separately.

In operation 204, the ultrasound imaging data and video stream are transmitted to a second location. The imaging data and video stream may be compressed before transmission to reduce bandwidth requirements.

In operation 206, the ultrasound imaging data and video stream are received and displayed at the second location. The ultrasound imaging data and video stream may be displayed simultaneously in dedicated areas of a remote user interface display. The ultrasound imaging data and video stream may be presented in a side-by-side format, or in a picture-in-picture format. Alternatively, the two video sources may be shown concurrently or toggled back and forth on demand by the remote expert.

In operation 208, a plurality of graphical elements corresponding to possible positional corrections of the probe are displayed at the second location.

In operation 210, the remote user interface device receives instructions on positional correction. This input may involve, for example, selection or dragging and dropping of the graphical elements displayed in operation 208.

In operation 212, the instructions on positional correction are transmitted to the first location.

In operation 214, the instructions on positional correction are output at the first location.

Figure 7:
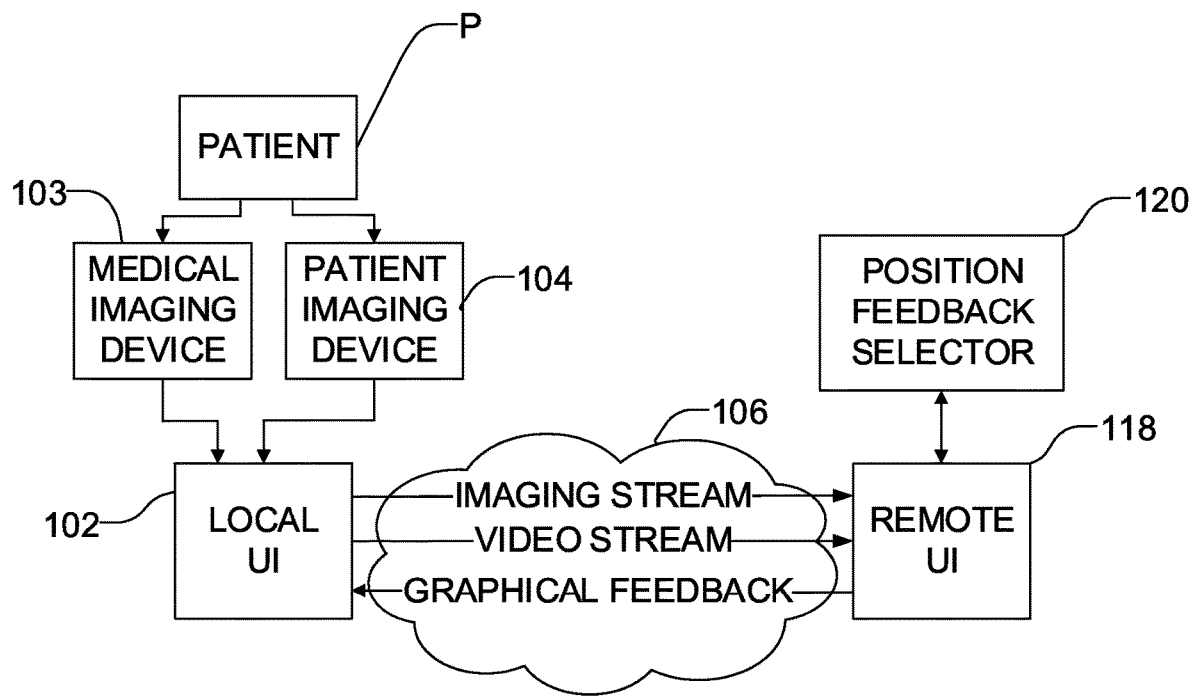
FIG. 7 is a schematic diagram of an alternative embodiment of an ultrasound system adapted to facilitate remote ultrasound feedback.

FIG. 7 is a schematic diagram depicting a remote ultrasound feedback system according to an alternative embodiment. In this embodiment, there is no two-way voice communication between the operator and the expert. The operator relies on the graphical feedback provided by the expert to adjust the operator's scan technique and capture the desired image. This embodiment may be particularly useful when the operator and expert do not speak the same language, or when network 106 is unable to support voice communication.

Example Embodiment

Figure 11:
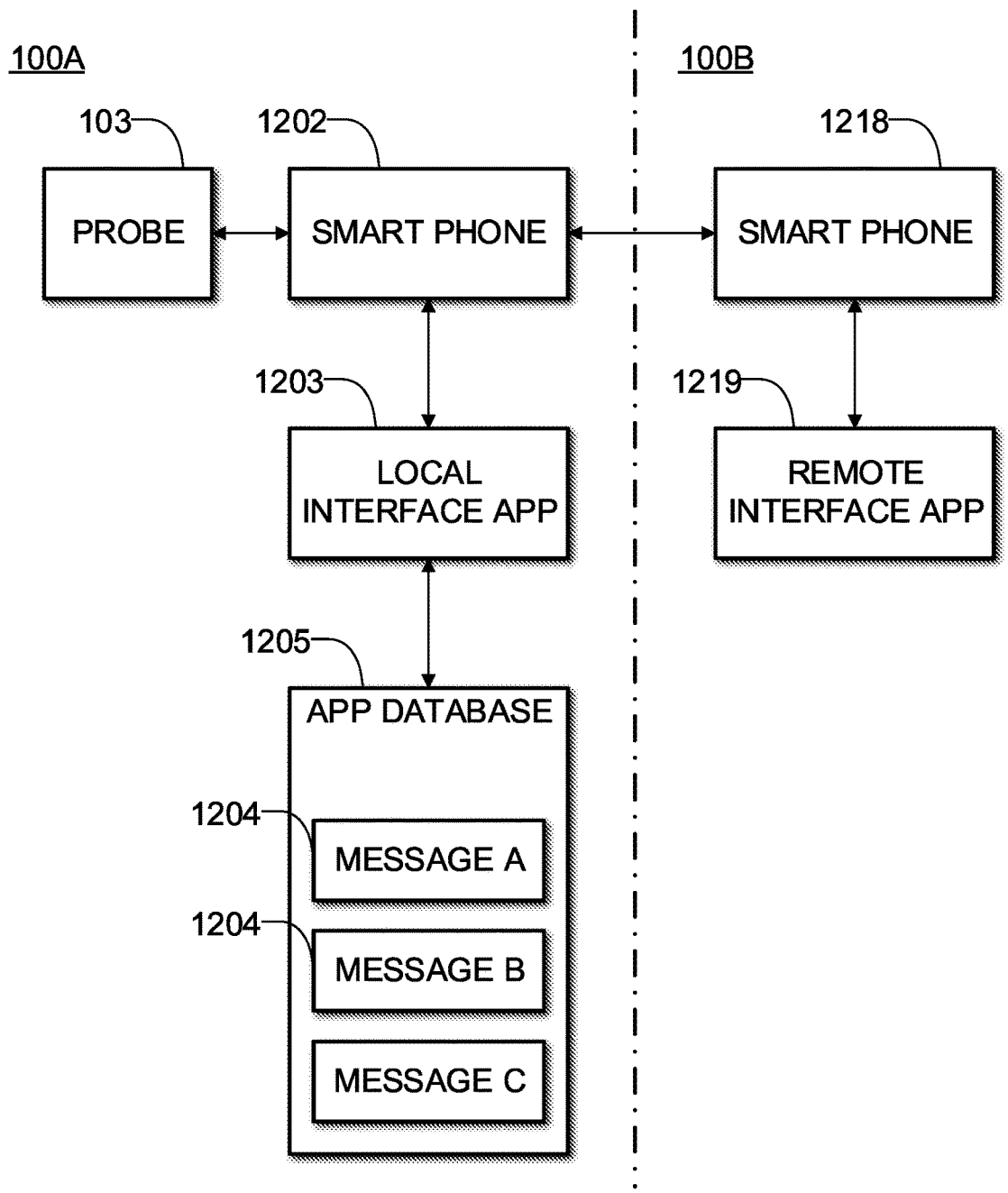
FIG. 11 depicts the use of apps on smart phones to provide elements of a system as described herein.

In some embodiments local user interface 102 and/or remote interface 118 are provided by general purpose computing devices. Such computing devices may execute software (e.g. apps) that cause them to provide functionality as described herein. FIG. 11 illustrates an example embodiment wherein local user interface 102 is provided by a cellular telephone 1202 configured with an app 1203 that includes predetermined messages 1204 in an app database 1205. Remote interface 118 is provided by a cellular telephone 1218 executing an app 1219. App 1219 provides controls that enable the expert to provide predetermined feedback messages to a user as described herein.

Interpretation of Terms

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;

the singular forms "a", "an", and "the" also include the meaning of any appropriate plural forms.

"remote" means not in the same location as. In some embodiments remote apparatus 100B may be a great distance away from local apparatus 100A (even in a different state, country or continent). In other embodiments remote apparatus 100B may be in the same building as local apparatus 100A.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different described embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An ultrasound imaging system comprising:
   a hand-holdable probe comprising:
      a transducer;
      transmit and receive circuits respectively operable to drive the transducer to transmit ultrasound energy to a patient and to receive signals generated by the transducer in response to ultrasound energy received from the patient; and an image processing circuit comprising a beamformer configured to process the received signals to yield ultrasound image data; and a local user interface device communicably coupled to the hand-holdable probe, the local user interface device configured to receive and display the ultrasound image data, and the local user interface device comprising:

an ultrasound image buffer configured to store a plurality of frames of the ultrasound image data;

a camera operable to generate a video stream;

a video stream buffer configured to store a plurality of frames of the video stream generated from the camera; and a data interface connected to transmit, to a remote interface, the plurality of frames of the ultrasound image data and the plurality of frames of the video stream generated from the camera, wherein the remote interface is configured to display a user interface comprising:

a palette of selectable controls that correspond to movements of the probe, the remote interface being configured to receive input selecting a selectable control of the selectable controls from the palette, wherein upon selecting the selectable control, the remote interface transmits a position correction message corresponding to the selectable control to the data interface, the position correction message relating to positional correction for the probe, and a freeze control, wherein upon actuation of the freeze control, the remote interface transmits to the data interface a freeze message that identifies both a selected one of the plurality of frames of the video stream generated by the camera and a selected one of the plurality of frames of the ultrasound image data; and a display connected to:

upon receipt of the position correction message, display the ultrasound image data with a positional correction symbol, the positional correction symbol being determined by the position correction message received from the remote interface, and upon receipt of the freeze message, display both the selected one of the plurality of frames of the video stream and the selected one of the plurality of frames of the ultrasound image data, so that a position and orientation of the probe for acquiring the selected one of the plurality of frames of the ultrasound image data is shown in the selected one of the plurality of frames of the video stream.

2. An ultrasound imaging system according to claim 1 wherein each of the selectable controls on the palette comprise a graphical element, the graphical element comprising a depiction of the probe and an arrow indicating a particular desired motion of the probe.

3. An ultrasound imaging system according to claim 2 wherein the positional correction symbol displayed on the display correspond to the graphical element on the selectable control selected at the remote interface.

4. An ultrasound imaging system according to claim 2 wherein the graphical element comprises:
an icon depicting tilting the probe forward;
an icon depicting tilting the probe backward;
an icon depicting rocking the probe right;
an icon depicting rocking the probe left;
an icon depicting rotating the probe clockwise; or
an icon depicting rotating the probe counter-clockwise.

5. An ultrasound imaging system according to claim 2 wherein the graphical element comprises:
an icon depicting moving the probe to the left;
an icon depicting moving the probe to the right;
an icon depicting moving the probe forward; or
an icon depicting moving the probe backward.

6. An ultrasound imaging system according to claim 1 wherein the local user interface device is configured to discontinue display of the positional correction symbol by fading the displayed positional control symbol a predetermined time after commencing display of the positional control symbol.

7. An ultrasound imaging system according to claim 1 wherein the probe comprises a motion sensor and is configured to determine from the motion sensor whether or not the probe is being moved in a way corresponding to the displayed positional control symbol, and the local user interface is configured to discontinue display of the positional correction symbol in response to determining from the motion sensor that the probe has been moved in the way corresponding to the displayed positional control symbol.

8. An ultrasound imaging system according to claim 7 wherein the probe or the local user interface device is configured to issue a warning signal in response to determining from the motion sensor that the probe has been not moved in the way corresponding to the displayed positional control symbol.

9. An ultrasound imaging system according to claim 2 wherein the graphical element comprises:
an icon depicting increasing pressure on the probe; or
an icon depicting decreasing pressure on the probe.

10. An ultrasound imaging system according to claim 9 comprising a pressure sensor arranged to measure a pressure on the probe.

11. An ultrasound imaging system according to claim 1 wherein the data interface is further configured: to receive a video freeze message by way of the remote interface, the video freeze message identifying a video frame of the plurality of frames of the video stream, and, in response to the video freeze message, the display displays the video frame.

12. An ultrasound imaging system according to claim 1 wherein the video stream depicts the probe, and the data interface is further configured: to receive from the remote interface an indication of an ending position for the probe, and the display displays an animation illustrating a motion of the probe from a current position of the probe to the ending position.

13. An ultrasound imaging system according to claim 1 wherein the data interface is further configured: to receive from the remote interface one or more annotations, and the display displays the one or more annotations.

14. An ultrasound imaging system according to claim 1, wherein the local user interface comprises a plurality of stored annotations and the local user interface device is configured: to receive from the remote interface by way of the data interface an annotation message identifying a selected one of the stored annotations and, in response, to retrieve and display the selected annotation on the display.

15. An ultrasound imaging system according to claim 1 wherein the probe comprises a directional indicator and the local user interface device is configured to operate the directional indicator on the probe to indicate a position correction corresponding to the position correction message.

16. An ultrasound imaging system according to claim 15 wherein the directional indicator comprises a display on the probe.

17. An ultrasound imaging system according to claim 15 wherein the directional indicator comprises a plurality of indicator lights on the probe.

18. An ultrasound imaging device according to claim 1 wherein the data interface is further configured: to receive an ultrasound image freeze message by way of the remote interface, the ultrasound image freeze message identifying an ultrasound image frame of the plurality of frames of the ultrasound image data, and, in response to the ultrasound freeze message, the display displays the ultrasound image frame.

19. An ultrasound imaging system according to claim 18 wherein the local user interface device is configured to display on the display the ultrasound image frame next to or as an overlay superposed on a live view of the ultrasound image data.

20. An ultrasound imaging system according to claim 1 further comprising a demonstration device equipped with a position sensor in communication with the remote interface wherein the remote interface is configured to transmit data comprising tracked positions and orientations of the demonstration device to the local user interface device and the local user interface device is configured to generate and display an animation corresponding to the tracked positions and orientations of the demonstration device.

21. An ultrasound imaging system according to claim 1 wherein the remote interface comprises a display configured to display the ultrasound image data and when receiving the input selecting the selectable control, the remote interface receives an input of dragging and dropping the selectable control onto the display of the ultrasound image data.

22. A method for providing positional feedback to an operator performing an ultrasound scan, the method comprising:
    acquiring a plurality of frames of ultrasound image data from a probe at a first location;
    acquiring a plurality of frames of a video stream depicting the probe and the patient at the first location;
    transmitting, from the first location to a second location that is remote from the first location, the plurality of frames of ultrasound image data and the plurality of frames of the video stream;
    displaying on a graphical interface at the second location the plurality of frames of ultrasound image data, the plurality of frames of the video stream, a palette of selectable controls that correspond to movements of the probe, and a freeze control;
    receiving input, through the graphical interface, that selects a selectable control of the selectable controls from the palette or that actuates the freeze control;
    upon selecting the selectable control from the palette,
        transmitting a position correction message corresponding to the selectable control from the second location to the first location, the position correction message relating to positional correction for the probe at the first location, and
        outputting a positional correction symbol determined by the position correction message to a display of a device at the first location; and
    upon actuation of the freeze control,
        transmitting a freeze message from the second location to the first location, the freeze message identifying both a selected one of the plurality of frames of the video stream and a selected one of the plurality of frames of the ultrasound image data, and
        outputting both the selected one of the plurality of frames of the video stream and the selected one of the plurality of frames of the ultrasound image data to a display of the device at the first location, so that a position and orientation of the probe for acquiring the selected one of the plurality of frames of the ultrasound image data is shown in the selected one of the plurality of frames of the video stream.

23. The method of claim 22, wherein receiving input through the graphical interface to select a selectable control comprises dragging and dropping the selectable control from the user interface on to a frame of the plurality of frames of the video stream.

24. The method of claim 22, wherein receiving input through the graphical interface to select a selectable control comprises dragging and dropping the selectable control from the user interface on to a frame of the plurality of frames of the ultrasound image data.

* * * * *